US008080549B2

(12) United States Patent
Harbeson

(10) Patent No.: US 8,080,549 B2
(45) Date of Patent: Dec. 20, 2011

(54) ENDOTHELIN RECEPTOR ANTAGONISTS

(75) Inventor: Scott L. Harbeson, Cambridge, MA (US)

(73) Assignee: CoNCERT Pharmaceuticals, Inc., Lexington, MA (US)

(*) Notice: Subject to any disclaimer, the term of this patent is extended or adjusted under 35 U.S.C. 154(b) by 6 days.

(21) Appl. No.: 12/460,575

(22) Filed: Jul. 20, 2009

(65) Prior Publication Data

US 2010/0063076 A1    Mar. 11, 2010

Related U.S. Application Data

(63) Continuation-in-part of application No. 12/008,698, filed on Jan. 11, 2008.

(60) Provisional application No. 60/884,654, filed on Jan. 12, 2007.

(51) Int. Cl.
*A01N 43/58* (2006.01)
*A61K 31/50* (2006.01)
*C07D 239/02* (2006.01)

(52) U.S. Cl. ........................................ 514/247; 544/242

(58) Field of Classification Search .................. 544/242; 514/247

See application file for complete search history.

(56) References Cited

U.S. PATENT DOCUMENTS

| | | | |
|---|---|---|---|
| 5,292,740 A | 3/1994 | Burri et al. | |
| 5,696,116 A | 12/1997 | Clozel et al. | |
| 5,846,514 A | 12/1998 | Foster et al. | |
| 5,945,448 A | 8/1999 | Ninomiya et al. | |
| 6,087,368 A | 7/2000 | Macor et al. | |
| 6,139,971 A | 10/2000 | Bruchlaus et al. | |
| 6,221,335 B1 | 4/2001 | Foster | |
| 6,440,710 B1 | 8/2002 | Keinan et al. | |
| 6,586,391 B1 | 7/2003 | Banting et al. | |
| 6,603,008 B1 | 8/2003 | Ando et al. | |
| 6,635,648 B2 | 10/2003 | Adams et al. | |
| 6,696,719 B2 | 2/2004 | Yamamoto | |
| 6,869,970 B2 | 3/2005 | Marti | |
| 7,019,013 B2 | 3/2006 | Eggenweiler et al. | |
| 7,208,602 B2 | 4/2007 | Pissarnitski et al. | |
| 7,517,990 B2 | 4/2009 | Ito et al. | |
| 2003/0144300 A1 | 7/2003 | Magee et al. | |
| 2004/0063719 A1 | 4/2004 | Adams et al. | |
| 2004/0063731 A1 | 4/2004 | Eggenweiler et al. | |
| 2006/0205733 A1 | 9/2006 | Dixon et al. | |
| 2007/0037831 A1 | 2/2007 | Cuffie-Jackson et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |
| 2009/0005394 A1 | 1/2009 | Harbeson | |
| 2009/0069351 A1 | 3/2009 | Czarnik | |

FOREIGN PATENT DOCUMENTS

| | | |
|---|---|---|
| WO | WO 95/26325 A2 | 10/1995 |
| WO | WO 96/38173 A1 | 5/1996 |
| WO | WO 01/05120 | 1/2001 |
| WO | WO 02/074034 | 9/2002 |
| WO | WO 2004/017993 | 3/2004 |
| WO | WO 2004/082637 | 9/2004 |
| WO | WO 2005/101608 | 10/2005 |
| WO | WO 2007/016361 A2 | 2/2007 |
| WO | WO 2007/118651 A1 | 10/2007 |
| WO | WO 2008/088727 A2 | 7/2008 |

OTHER PUBLICATIONS

Hopfgartner, G., "Fragmentation of Bosentan® (Ro 47/0203) in Ionspray Mass Spectrometry After Collision-induced Dissociation at Low Energy: a Case of Radical Fragmentation of an Even-electron Ion," *Journal of Mass Spectrometry*, 31:69-76 (1996).

Lausecker, B. and Hopfgartner, G., "Determination of an Endothelin Receptor Antagonist in Human Plasma by Narrow-bore Liquid Chromatography and Ionspray Tandem Mass Spectrometry," *Journal of Chromatography*, 712(1):75-83 (1995).

Lausecker, B., and Fischer, G., "Development of a Liquid Chromatographic/Tandem Mass Spectrometric Assay for a new Endothelin Receptor Antagonist, and its Application to Dog Plasma Samples Generated After Simultaneous I.V. and P.O. Administration of the Unlabeled and Deuterium-Labeled Forms of this Antagonist," *Journal of Mass Spectrometry*, 38(6):649-658 (2003).

Gideon, Paul A., et al., "Bosentan Decreases the Plasma Concentration of Sildenafil when Coprescribed in Pulmonary Hypertension," *British Journal of Clinical Pharmacology*, 60(1):107-112, (2005).

Fisher, M.B. et al., "The Complexities Inherent in Attempts to Decrease Drug Clearance by Blocking Sites of CYP-Mediated Metabolism," *Curr. Opin. Drug Discov.*, 9(1): 101-109 (Jan. 2006).

Kushner, D.J. et al., "Pharmacological Uses and Perspectives of Heavy Water and Deuterated Compounds," *Can. J. Physiol. Pharmacol.*, 77(2): 79-88 (Feb. 1999).

Prescribing Information for TRACLEER® (bosentan), NDA 21-290/S-006 and S-007, pp. 3-22 (month not available).

Harrington, P.J., et al., Org. Process R&D 2002, 6(2), 120.

International Search Report dated Sep. 17, 2008, issued in PCT/US2008/000384.

Written Opinion of the International Searching Authority dated Sep. 17, 2008, issued in PCT/US2008/000384.

Notification Concerning Transmittal of International Preliminary Report on Patentability, International Application No. PCT/US2008/000384, Date of Mailing Jul. 23, 2009.

Baillie, T. A., "The Use of Stable Isotopes in Pharmacological Research," *Pharmacological Reviews*, 33(2): 81-132 (1981).

Browne, T. R., "Stable Isotope Techniques in Early Drug Development: An Economic Evaluation," *J. Clin. Pharmacol.*, 38: 213-220 (1998).

(Continued)

*Primary Examiner* — Paul V. Ward
(74) *Attorney, Agent, or Firm* — Hamilton, Brook, Smith & Reynolds, P.C.

(57) ABSTRACT

This invention relates to novel endothelin receptor antagonists, derivatives, acceptable acid addition salts thereof. The invention also provides compositions comprising a compound of this invention and the use of such compositions in methods of treating diseases and conditions that are beneficially treated by compounds that block the endothelin signaling pathway that leads to vasoconstriction and in particular those diseases or conditions beneficially treated by endothelin receptor antagonists.

19 Claims, 1 Drawing Sheet

OTHER PUBLICATIONS

Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).

Dyck, L. E., et al., "Effects of Deuterium Substitution on the Catabolism of β-Phenylethylamine: An in Vivo Study," *Journal of Neurochemistry*, 46(2): 399-404 (1986).

Foster, A. B., "Deuterium Isotope Effects in Studies of Drug Metabolism," *Trends in Pharmacological Sciences*, 5: 524-527 (1984).

Foster, A. B., "Deuterium Isotope Effects in the Metabolism of Drugs and Xenobiotics: Implications for Drug Design," *Advances in Drug Research*, 14: 1-40 (1985).

Gouyette, A., "Synthesis of Deuterium-labelled Elliptinium and its Use in Metabolic Studies," *Biomedical and Environmental Mass Spectrometry*, 15: 243-247 (1988).

Haskins, N. J., "The Application of Stable Isotopes in Biomedical Research," *Biomedical Mass Spectrometry*, 9(7): 269-277 (1982).

Honma S., et al., "The Metabolism of Roxatidine Acetate Hydrochloride," *Drug Metabolism and Disposition*, 15(4): 551-559 (1987).

Pieniaszek, H. J., et al., "Moricizine Bioavailability via Simultaneous, Dual, Stable Isotope Administration: Bioequivalence Implications," *J. Clin. Pharmacol*, 39: 817-825 (1999).

Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).

Ubeaud, G., "Bosentan, a New Endothelin Receptor Antagonist: Prediction of the Systemic Plasma Clearance in Man From Combined in vivo and in vitro Data," *Xenobiotica*, 25(12): 1381-1390 (1995).

Wolen, R. L., "The Application of Stable Isotopes to Studies of Drug Bioavailability and Bioequivalence," *J. Clin. Pharmacol.*, 26: 419-424 (1986).

Park, B.K., et al., "Metabolism of Fluorine-Containing Drugs," *Annu. Rev. Pharmacol. Toxicol.*, 41:443-470 (2001).

Office Action, U.S. Appl. No. 12/008,698, Date of Mailing: Sep. 24, 2010.

Office Action, U.S. Appl. No. 12/008,698, Date of Mailing: Jun. 2, 2011.

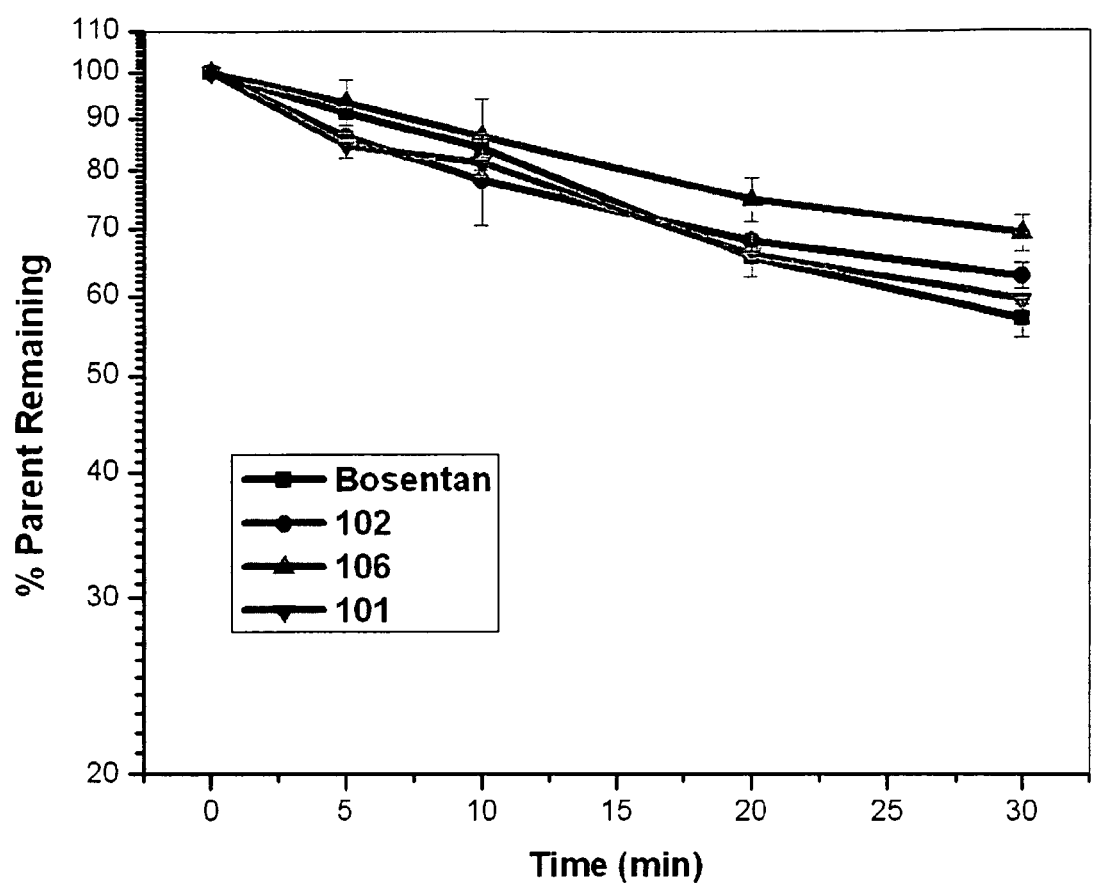

ENDOTHELIN RECEPTOR ANTAGONISTS

RELATED APPLICATIONS

This application is a continuation-in-part of U.S. application Ser. No. 12/008,698, filed Jan. 11, 2008, which claims the benefit of U.S. Provisional Patent Application No. 60/884,654, filed Jan. 12, 2007. The entire teachings of the above applications are incorporated herein by reference.

BACKGROUND OF THE INVENTION

Bosentan is known by the chemical names N[6-(2-hydroxyethoxy)-5-(2-methoxyphenoxy)-2-pyrimidin-2-yl-pyrimidin-4-yl]-4-tert-butyl-benzenesulfonamide and 4-tert-butyl-N[6-(2-hydroxy-ethoxy)-5-(2-methoxy-phenoxy)[2,2']-bipyrimidin-4-yl]-benzenesulfonamide.

Bosentan is a tetrasubstituted pyrimidine derivative that was reported in U.S. Pat. No. 5,292,740 to be useful for treating circulatory disorders, such as hypertension. Bosentan is now known to be a dual endothelin receptor antagonist that blocks the binding of endothelin to both the $ET_A$ and $ET_B$ receptors.

Endothelin-1 (ET-1), a 21-amino acid peptide neurohormone, was first isolated and described in 1998 and is an extremely potent and long-acting vasoconstrictor (Itoh, Y et al., FEBS Lett, 1988, 231:440). ET-1 causes vasoconstriction by binding to $ET_A$ and $ET_B$, which are receptors in the endothelium and vascular smooth muscle. ET-1 levels are elevated in the plasma and lung tissue of patients with pulmonary arterial hypertension, which suggests that ET-1 has a pathogenic role in this disease. Bosentan is believed to work by competitively and specifically binding to $ET_A$ and $ET_B$ receptor sites in the endothelium and vascular smooth muscle with a slightly higher affinity for $ET_A$ than for $ET_B$. This binding inhibits ET-1 from binding to $ET_A$ and/or $ET_B$, which interferes with a signaling pathway that is responsible for causing vasoconstriction.

Bosentan has been approved by the U.S. Food and Drug Administration to treat the symptoms of pulmonary arterial hypertension, high blood pressure within the main artery that carries blood from the heart's right ventricle to the lungs. Bosentan has been shown to be effective in decreasing the constriction of this artery, thereby increasing the supply of blood to the lungs and reducing the workload incurred by the heart.

Bosentan has been reported to have a half-life in humans of approximately five hours and is eliminated mainly through hepatic metabolism, followed by biliary excretion of three metabolites (see Center for Drug Evaluation and Research Approval Package for Application Number 21-290; Clinical Pharmacology and Biopharmaceutics Review; Aug. 16, 2001). One of these metabolites, hydroxybosentan, is active and responsible for up to 20% of the overall pharmaceutical properties of bosentan.

Bosentan is typically administered twice per day due to its short half-life. Multiple dosing can lead to compliance problems such as missed doses and overdosing when compensating for missed doses. Moreover, bosentan may cause liver damage due to bilary excretion and birth defects if taken during pregnancy. Thus, bosentan cannot be safely administered to patients who are pregnant or who suffer from liver impairment. Less serious side-effects of bosentan include headache, nasopharyngitis, flushing, edema of the lower limbs, hypotension, and palpitations. Bosentan may also decrease the effectiveness of hormonal contraceptives, regardless of the route of administration. Bosentan may also irreversibly lower sperm count in some men. These side effects may be attributable to one or more of the metabolites of bosentan and/or overdosing due to poor compliance.

Despite the beneficial activities of bosentan, there is a continuing need for new compounds to treat the aforementioned diseases and conditions.

SUMMARY OF THE INVENTION

This invention relates to novel endothelin receptor antagonists, derivatives, and pharmaceutically acceptable acid addition salts thereof. The invention also provides compositions comprising a compound of this invention and the use of such compositions in methods of treating diseases and conditions that are beneficially treated by compounds that block the endothelin signaling pathway that leads to vasoconstriction and in particular those diseases or conditions beneficially treated by endothelin receptor antagonists.

BRIEF DESCRIPTION OF THE DRAWINGS

The FIGURE is a graph showing the percent of compound remaining versus time post incubation of Bosentan, Compound 102, Compound 106 and Compound 101 with CYP3A4 supersomes.

DETAILED DESCRIPTION OF THE INVENTION

Definitions

The terms "ameliorate" and "treat" are used interchangeably and both mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of bosentan will inherently contain small amounts of deuterated isotopologues. The concentration of naturally abundant stable hydrogen isotopes, notwithstanding this variation, is small and immaterial with respect to the degree of stable isotopic substitution of compounds of this invention. See for instance Wada E et al., Seikagaku 1994, 66:15; Gannes L Z et al., Comp Biochem Physiol Mol Integr Physiol 1998, 119:725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiment, a compound of the invention, contains less than 10%, preferably less than 6%, and more preferably less than 3% of all other isotopologues combined, including a form that lacks any deuterium. In certain aspects, the compound contains less than "X" % of all other isotopologues combined, including a form that lacks any deuterium; where X is any number between 0 and 10 (e.g., 1, 0.5, 0.001) inclusive. Compositions of matter that contain greater than 10% of all other isotopologues combined are referred to herein as "mixtures" and must meet the parameters set forth below. These limits of isotopic composition and all references to isotopic composition herein, refer solely to the relative amounts of deuterium/hydrogen present in the active, free base form of the compound of Formula I, and neither includes the isotopic composition of counterions, or of any other atoms.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The term "isotopologue" refers to a species that differs from a specific compound of this invention only in the isotopic composition thereof or of its ions.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 55% of the compound.

The invention also provides salts of the compounds of the invention.

A salt of a compound of this invention is formed between an acid and a basic group of the compound, such as an amino functional group or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention may contain one or more asymmetric carbon atoms. As such, a compound of this invention can exist as the individual stereoisomers (enantiomers or diastereomers) as well a mixture of any possible stereoisomers. Accordingly, a compound of the present invention will include not only a stereoisomeric mixture, but also individual respective stereoisomers that are substantially free from other stereoisomers. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "tert" refers to tertiary. "Bu" refers to t-butyl.

Throughout this specification, a variable may be referred to generally (e.g., "each Y") or may be referred to specifically (e.g., $Y^{1a}, Y^{1b}, Y^{1c}, Y^{2a}, Y^{2b}, Y^{2c}, Y^{2d}$, etc.). Unless otherwise indicated, when a variable is referred to generally, it is meant to include all specific embodiments of that particular variable.

Therapeutic Compounds

The present invention provides a compound of Formula I:

(I)

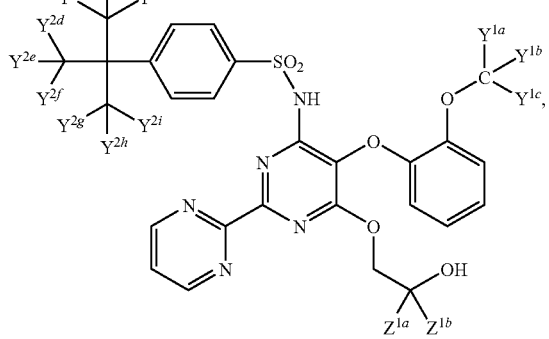

or a pharmaceutically acceptable salt thereof, wherein:

each Y is independently selected from hydrogen and deuterium, and $Y^{2a}$ is additionally selected from OH;

each Z is independently selected from hydrogen, deuterium, and fluorine; and at least one Y or Z is deuterium.

In one embodiment, each Y is the same. In a more specific embodiment, $Y^{1a}$, $Y^{1b}$ and $Y^{1c}$ are simultaneously deuterium.

In another embodiment, $Y^{2b}$, $Y^{2c}$ $Y^{2d}$, $Y^{2e}$, $Y^{2f}$ $Y^{2g}$, $Y^{2h}$, $Y^{2i}$ are the same. In still another embodiment, $Y^{2a}$, $Y^{2b}$, $Y^{2c}$ $Y^{2d}$, $Y^{2e}$, $Y^{2f}$, $Y^{2g}$, $Y^{2h}$, $Y^{2i}$ are the same.

In another embodiment, $Y^{1a}$, $Y^{1b}$ and $Y^{1c}$ are simultaneously deuterium and $Y^{2a}$, $Y^{2b}$, $Y^{2c}$ $Y^{2d}$, $Y^{2e}$, $Y^{2f}$, $Y^{2g}$, $Y^{2h}$, $Y^{2i}$ are simultaneously hydrogen.

In another embodiment, $Y^{1a}$, $Y^{1b}$ and $Y^{1c}$ are simultaneously deuterium; $Y^{2a}$ is OH; and $Y^{2b}$, $Y^{2c}$ $Y^{2d}$, $Y^{2f}$, $Y^{2g}$, $Y^{2h}$, $Y^{2i}$ are simultaneously hydrogen.

In another embodiment, $Y^{2a}$, $Y^{2b}$ and $Y^{2c}$ are simultaneously deuterium.

In another embodiment, $Y^{2b}$ and $Y^{2c}$ are simultaneously deuterium; and $Y^{2a}$ is OH.

In another embodiment, $Y^{2a}$, $Y^{2b}$, $Y^{2c}$ $Y^{2d}$, $Y^{2e}$ and $Y^{2f}$ are simultaneously deuterium.

In another embodiment, $Y^{2b}$, $Y^{2c}$ $Y^{2d}$, $Y^{2e}$ and $Y^{2f}$ are simultaneously deuterium; and $Y^{2a}$ is OH.

In another embodiment, $Y^{2a}$, $Y^{2b}$, $Y^{2c}$ $Y^{2d}$, $Y^{2e}$, $Y^{2f}$, $Y^{2g}$, $Y^{2h}$, $Y^{2i}$ are simultaneously deuterium.

In another embodiment, $Y^{2b}$, $Y^{2c}$ $Y^{2d}$, $Y^{2e}$, $Y^{2f}$ $Y^{2g}$, $Y^{2h}$, $Y^{2i}$ are simultaneously deuterium; and $Y^{2a}$ is OH.

In another embodiment, each Z is the same.

In another embodiment each of $Z^{1a}$ and $Z^{1b}$ are independently selected from fluorine and deuterium. In a more specific embodiment, $Z^{1a}$ and $Z^{1b}$ are simultaneously deuterium.

In another embodiment, each $Y^{1}$ is the same, each of $Y^{2b}$, $Y^{2c}$ $Y^{2d}$, $Y^{2e}$, $Y^{2f}$, $Y^{2g}$, $Y^{2h}$, $Y^{2i}$ is the same; each Z is the same, and the compound (Cmpd) is selected from any one of the compounds described in Table 1 (below).

TABLE 1

Description of Exemplary Compounds of This Invention

| Cmpd | Each $Y^{1}$ | $Y^{2a}$ | $Y^{2b}$-$Y^{2i}$ | Each Z |
|------|------|------|------|------|
| 100 | D | H | H | D |
| 101 | D | D | D | H |
| 102 | D | H | H | H |
| 103 | H | D | D | H |
| 104 | H | H | H | D |
| 105 | H | D | D | D |
| 106 | D | D | D | D |
| 107 | D | OH | H | D |
| 108 | D | OH | D | H |
| 109 | D | OH | H | H |
| 110 | H | OH | D | H |
| 111 | H | OH | H | D |
| 112 | H | OH | D | D |
| 113 | D | OH | D | D |
| 114 | D | H | H | F |
| 115 | D | D | D | F |
| 116 | H | D | D | F |
| 117 | D | OH | H | F |
| 118 | D | OH | D | F |
| 119 | H | OH | D | F |

In another set of embodiments, any atom not designated as deuterium in any of the embodiments set forth above is present at its natural isotopic abundance.

In an even more specific embodiment, the compound of Formula I is selected from:

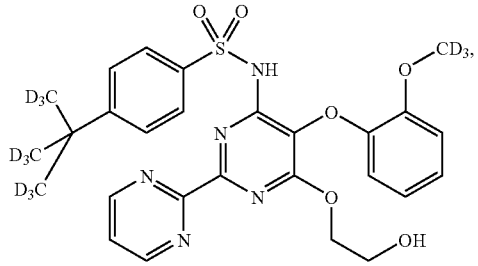

Compound 101

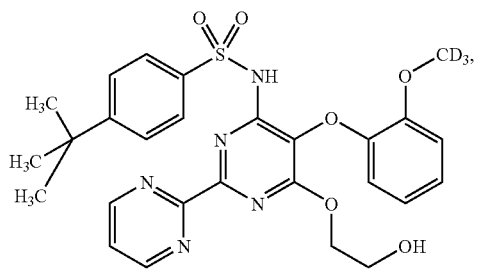

Compound 102

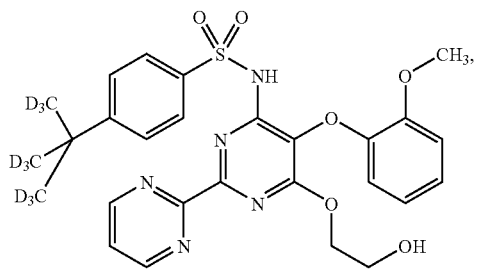

Compound 103

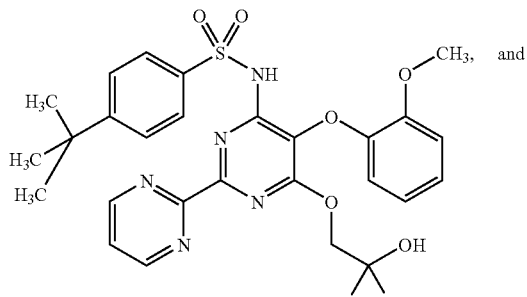

Compound 104

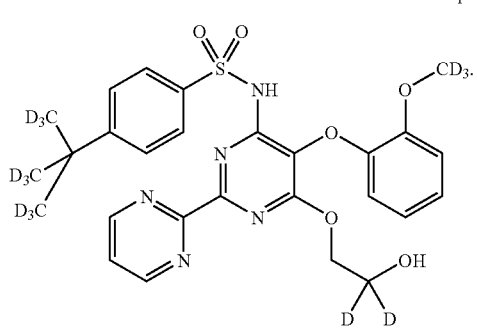

Compound 106

The synthesis of compounds of the formulae herein (e.g., Formula I) can be readily achieved by synthetic chemists of ordinary skill. Relevant procedures and intermediates are disclosed, for instance, in U.S. Pat. Nos. 5,292,740 and 6,139,971; PCT patent publication WO2001005120; and Harrington, P J et al., Org Process Res Dev, 6(2): 120. Such methods can be carried out utilizing corresponding deuterated reagents to synthesize the compounds delineated herein, or invoking standard synthetic protocols known in the art for introducing isotopic atoms to a chemical structure.

Exemplary Synthesis

A convenient method for producing compounds of the formulae herein (e.g., Formula I) is illustrated in Scheme 1.

Scheme 1:
General Method for Synthesizing Compounds of Formula I.

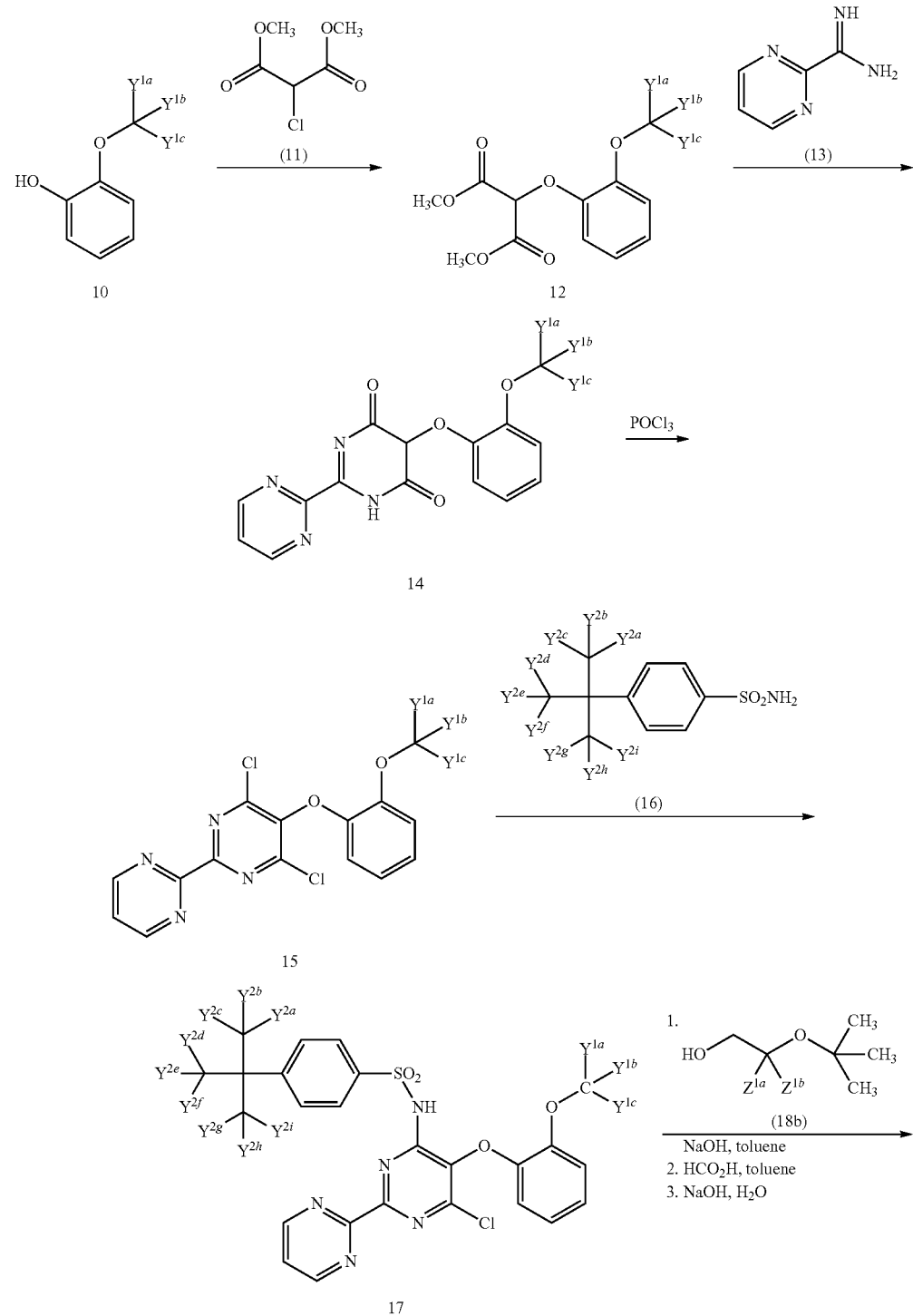

-continued

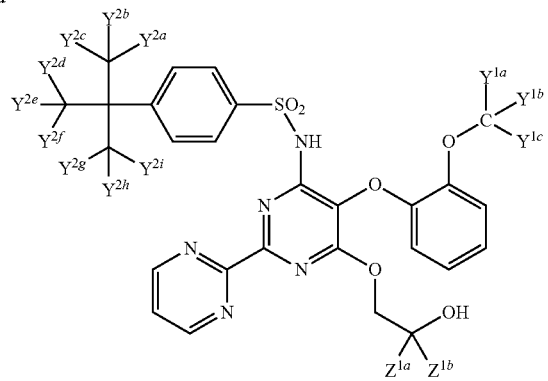

(I)

The exemplary synthesis depicted in Scheme 1 involves condensation of 2-chloromalonic acid dimethyl ester 11 with an appropriately deuterated guaiacol 10 to afford the 2-(2-methoxyphenoxy)malonic acid dimethyl ester 12, followed by cyclization of 12 with 13 to afford the corresponding bipyrimidinedione 14. This compound 14 is treated with refluxing $POCl_3$ to afford the dichlorobipyrimidine 15, which is subsequently treated with an appropriately deuterated 4-tert-butylphenylsulfonamide 16, $K_2CO_3$ and tetrabutylammonium bromide (TBAB) in toluene to provide the monosubstituted sulfonamide 17. Compound 17 is thereafter treated with an appropriately deuterated or fluorinated ethyleneglycol mono-tert-butyl ether 18b and NaOH in hot toluene to afford the tert-butyl ether protected intermediate, which is thereafter deprotected by reaction with formic acid to afford the formate ester. This ester is then hydrolyzed with NaOH in a mixture of water and ethanol, to afford the target compounds of Formula I. Such compounds of Formula I are readily purified by crystallization, comprising heating the crude product into a mixture of ethanol and water to afford a solution and thereafter allowing the solution to cool. Other approaches to synthesizing compounds of the formulae herein (e.g., Formula I) can readily be adapted from references cited herein. Variations of these procedures and their optimization are within the skill of the ordinary practitioner.

An appropriately deuterated 4-tert-butylphenylsulfonamide 16 can be synthesized as in Scheme 2.

Scheme 2:
synthesis of Appropriately-Deuterated Intermediate 16.

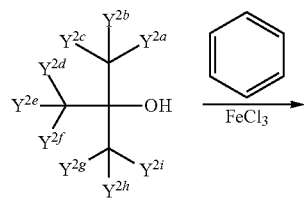

19

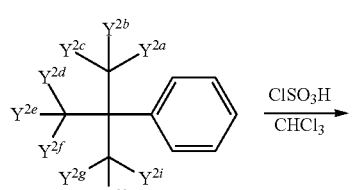

20

-continued

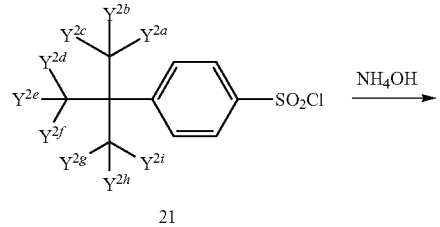

21

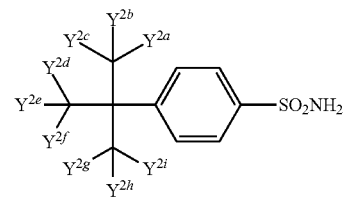

16

An appropriately deuterated tert-butanol 19, such as commercially available d9-tert-butanol, is reacted with benzene in the presence of ferric chloride (see Potts, W M et al., J Am Chem Soc, 1939, 61: 2553) to provide 20, which is then reacted with chlorosulfonic acid to provide the sulfonyl chloride 21 (Gayen, S et al., Internet Electronic J Mol Design, 2005, 4: 556). The sulfonyl chloride is converted to the sulfonamide 16 according to the method of Morimoto, H et al., J Med Chem, 2001, 44: 3355. Although not shown in Scheme 2, the sulfonic acid analog of compound 21 (compound 23) is readily available via hydrolysis of 21 in aqueous dioxane according to the method of Tonnet, M L et al., Aus J Chem, 1971, 24: 703.

Appropriately-deuterated ethyleneglycol mono-tert-butyl ethers 18 and 18a may be prepared as shown in Schemes 3a and 3b.

Scheme 3a:
Synthesis of Intermediate 18.

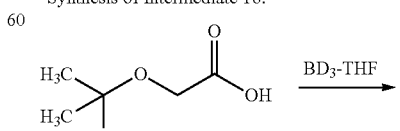

23

-continued

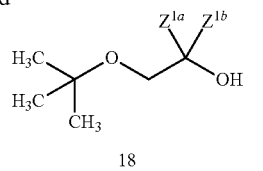

18

Commercially available 2-tert-butoxyacetic acid (22) is reduced with d3-borane according to the method of Yoon, N M et al., J Org Chem, 1973, 38: 2786 to produce the corresponding deuterated ethyleneglycol mono-tert-butyl ether 18.

Scheme 3b:
Synthesis of Intermediate 18a.

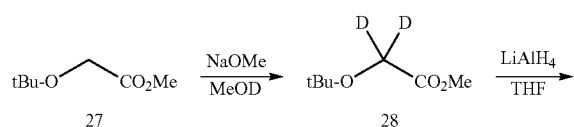

-continued

18a

Treatment of commercially available methyl 2-tert-butoxyacetate (27) with NaOMe in MeOD to produce the corresponding deuterated methyl 2-tert-butoxyacetate (28) followed by reduction with LiAlH$_4$ affords the ethyleneglycol mono-tert-butyl ether 18a, a deuterated example of intermediate 18b.

An alternate route to a compound of Formula I, wherein each Z is deuterium is shown in Scheme 4.

Scheme 4:
Alternate Synthetic Route to Compounds of Formula I wherein Z = D.

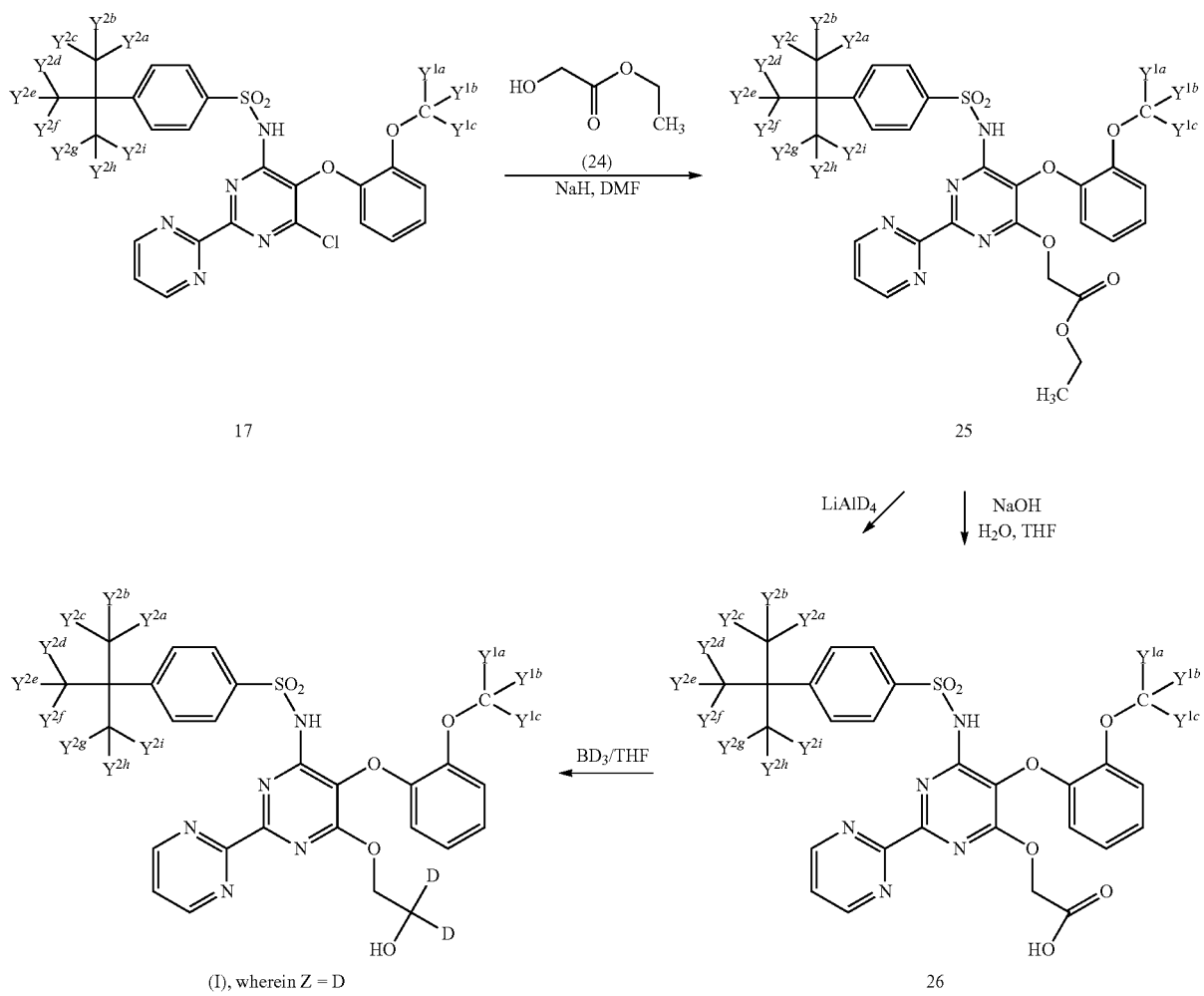

The appropriately deuterated sulfonamide 17 from Scheme 1 is treated with ethyl 2-hydroxyacetate (24) to produce the corresponding ester 25 according to the method of Harada, H et al., Chem Pharm Bull, 2001, 49: 606-612. The ester 25 is hydrolyzed to the corresponding acid 26, which is then reduced with deuterodiborane in THF to the deuterated compound of Formula I. Alternatively, the ester 25 may be reduced directly to the deuterated compound of Formula I by treatment with $LiAlD_4$.

Certain intermediates that are useful for preparing compounds of Formula I are new. Accordingly, other embodiments of this invention relate to a compound of any one of formulae 12, 14, 15, 16, 17, 18b, 21 or 23 shown in Schemes 1-3b.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (e.g., $Y^{1a}, Y^{1b}, Y^{1c}, Y^{2a}, Y^{2b}, Y^{2c}, Y^{2d}, Y^{2e}, Y^{2f}, Y^{2g}, Y^{2h}, Y^{2i}, Z^{1a}$ and $Z^{2b}$) or not. The suitability of a chemical group in a compound structure for use in synthesis of another compound structure is within the knowledge of one of ordinary skill in the art.

Additional methods of synthesizing compounds of the formulae herein (e.g., Formula I) and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Combinations of substituents and variables envisioned by this invention are only those that result in the formation of stable compounds.

The invention further provides a mixture of a compound of this invention and its lighter isotopologues. These mixtures may occur, for instance, simply as the result of an inefficiency of incorporating the isotope at a given position; intentional or inadvertent exchange of protons for deuterium, e.g. exchange of bulk solvent for heteroatom-attached deuterium; or intentional mixtures of pure compounds.

In one embodiment, such mixtures comprise at least about 50% of the heavy atom isotopic compound (i.e., less than about 50% of lighter isotopologues). More preferable is a mixture comprising at least 80% of the heavy atom isotopic compound. Most preferable is a mixture comprising 90% of the heavy atom isotopic compound. In one aspect, is a mixture at least about "X"% of the heavy atom isotopic compound (i.e., less than about X % of lighter isotopologues), where X is a number between 0 and 100, inclusive.

Compositions

The invention also provides compositions comprising an effective amount of a compound of Formula I (e.g., including any of the formulae herein), or a pharmaceutically acceptable salt thereof; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of the present invention further comprises a second therapeutic agent. The second therapeutic agent includes any compound or therapeutic agent known to have or that demonstrates advantageous properties when administered with an endothelin antagonist. Such agents are the same as those indicated as useful in combination with bosentan, including, but not limited to those described in U.S. Pat. Nos. 6,635,648; 6,586,391; 6,869,970; 5,945,448; and 5,696,116; and in PCT patent publications WO 2005101608; WO 2004082637; WO 2004017993; and WO 2002074034. Preferably, the second therapeutic agent is an agent useful in the treatment or prevention of a disease or condition selected from pulmonary arterial hypertension, erectile dysfunction, chronic obstructive pulmonary disease, chronic pelvic pain syndrome type III, primary dysmenorrhea, pre-eclampsia, thalassemia, skin fibrosis, hypertension, hypoxia-induced pulmonary artery hypertension, interstitial lung disease, scleroderma, idiopathic pulmonary fibrosis, pulmonary hypertension, chronic thromboembolic pulmonary hypertension, Eisenmenger's syndrome, benign prostatic hyperplasia, high blood pressure, coronary disorders, cardiac insufficiency, renal cerebral ischemia, cardiac infarct, migraine, subarachnoid haemorrhage, Raynaud syndrome, skin cancer, atherosclerosis, sickle cell disease, digital ulcers, and others, including, but not limited to those disclosed in U.S. Pat. No. 6,635,648; U.S. Pat. No. 5,292,740; U.S. Pat. No. 6,586,391; U.S. Pat. No. 6,869,970; U.S. Pat. No. 5,945,448; U.S. Pat. No. 5,696,116; WO 2005101608; WO 2004082637; WO 2004017993; WO 2002074034; and WO 9638173A1.

In one embodiment, the second therapeutic agent is selected from a prostacyclin, a prostacyclin derivative, a second endothelin antagonist, a dopaminergic agonist, a phosphodiesterase inhibitor, a sympathetic nervous system antagonist, an inhibitor of endothelin converting enzyme, an antihypertensive, an alpha-adrenergic blocker, or an angiotensin II receptor antagonist.

In another embodiment, the second therapeutic agent is selected from a phosphodiesterase inhibitor, such as sildenafil.

In another embodiment, the second therapeutic agent is selected from a prostacyclin or prostacyclin derivative, such as epoprostenol, treprostinil, iloprost, or beraprost.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537. An effective amount of a compound of this invention to be administered to a normal adult human can range from about 1 mg to about 1000 mg/day, more preferably from about 5 mg to about 500 mg/day, more preferably from about 25 mg/ to about 250 mg/day. Daily amounts of a compound of this invention will be administered in from one to about nine unit dosages per day. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a disease that is beneficially treated by bosentan comprising the step of administering to a subject in need thereof an effective amount of a compound or a composition of this invention. Such conditions and diseases are well known in the art and include but are not limited to pulmonary arterial hypertension, erectile dysfunction, chronic obstructive pulmonary disease, chronic pelvic pain syndrome type III, primary dysmenorrhea, pre-eclampsia, thalassemia, skin fibrosis, hypertension, hypoxia-induced pulmonary artery hypertension, interstitial lung disease, scleroderma, idiopathic pulmonary fibrosis, pulmonary hypertension, chronic thromboembolic pulmonary hypertension, Eisenmenger's syndrome, benign prostatic hyperplasia, high blood pressure, coronary disorders, cardiac insufficiency, renal cerebral ischemia, cardiac infarct, migraine, subarachnoid haemorrhage, Raynaud syndrome, skin cancer, atherosclerosis, sickle cell disease, and digital ulcers.

In a more specific embodiment, the method of this invention is used to treat a subject suffering from or susceptible to a disease or condition selected from pulmonary arterial hypertension, erectile dysfunction, skin fibrosis, interstitial lung disease, scleroderma, chronic thromboembolic pulmonary hypertension, Eisenmenger's syndrome, skin cancer, sickle cell disease, digital ulcers.

In an even more specific embodiment, the method of this invention is used to treat a subject suffering from or susceptible to a disease or condition selected from pulmonary hypertension (including pediatric subjects, subjects with class II disease who are mildly symptomatic, patients with sickle cell anemia, and patients with chronic thromboembolic pulmonary hypertension), idiopathic pulmonary fibrosis, digital ulcerations in patients with scleroderma, and interstitial lung disease in patients with scleroderma.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, the invention provides a method of modulating the interaction between ET-1 and its receptors in a cell, said modulation comprising contacting a cell with one or more compounds of any of the formulae herein.

In another embodiment, the above method of treatment comprises the further step of co-administering to the patient one or more second therapeutic agents. The choice of second therapeutic agent may be made from any second therapeutic agent known to be useful for co-administration with bosentan. Examples of such agents and the conditions and diseases for which each may be used in conjunction with a compound of this invention are described in PCT publications WO 04017993A1 and WO 9638173A1. Preferably, the second therapeutic agent is an agent useful in the treatment or prevention of a disease or condition selected from pulmonary arterial hypertension, brain edema or Eisenmenger's syndrome.

In one embodiment, the second therapeutic agent is selected from a prostacyclin or a prostacyclin analogue and the condition treated is pulmonary arterial hypertension. In a more specific embodiment, the prostacyclin or prostacyclin analogue is selected from epoprostenol, treprostinil, iloprost, or beraprost.

In another embodiment, the second therapeutic agent is a phosphodiesterase V inhibitor and the condition treated is selected from pulmonary arterial hypertension and Eisenmenger's syndrome. In a more specific embodiment, the phosphodiesterase V inhibitor is sildenafil.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy *Handbook,* 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of formula I alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

Diagnostic Methods and Kits

The compounds and compositions of this invention are also useful as reagents in methods for determining the concentration of bosentan in solution or biological sample such as plasma, examining the metabolism of bosentan and other analytical studies.

According to one embodiment, the invention provides a method of determining the concentration, in a solution or a biological sample, of bosentan, comprising the steps of:

a) adding a known concentration of a compound of Formula I to the solution of biological sample;

b) subjecting the solution or biological sample to a measuring device that distinguishes bosentan from a compound of Formula I;

c) calibrating the measuring device to correlate the detected quantity of the compound of Formula I with the known concentration of the compound of Formula I added to the biological sample or solution; and d) measuring the quantity of bosentan in the biological sample with said calibrated measuring device; and e) determining the concentration of bosentan in the solution of sample using the correlation between detected quantity and concentration obtained for a compound of Formula I.

Measuring devices that can distinguish bosentan from the corresponding compound of Formula I include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a patient following administration of the compound of Formula I. This method comprises the steps of obtaining a serum, urine or feces sample from the patient at a period of time following the administration of the compound of Formula I to the subject; and comparing the amount of the compound of Formula I with the metabolic products of the compound of Formula I in the serum, urine or feces sample.

The present invention also provides kits for use to treat a condition or disease selected from pulmonary arterial hypertension, scleroderma, chronic thromboembolic pulmonary hypertension, and idiopathic pulmonary fibrosis. These kits comprise (a) a pharmaceutical composition comprising a compound of Formula I or a salt thereof; or a prodrug, or a salt of a prodrug thereof; or a or polymorph thereof, wherein said pharmaceutical composition is in a container; and (b) instructions describing a method of using the pharmaceutical composition to treat a condition or disease selected from pulmonary arterial hypertension, scleroderma, chronic thromboembolic pulmonary hypertension, and idiopathic pulmonary fibrosis.

The container may be any vessel or other sealed or sealable apparatus that can hold said pharmaceutical composition. Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In an embodiment of the kits of this invention, the composition comprising the second active agent may be in a vessel or container that is separate from the vessel containing the composition comprising a compound of Formula I.

SYNTHETIC EXAMPLES

Example 1

Synthesis of 4-(tert-Butyl-d$_9$)-N-(6-chloro-5-(2-methoxyphenoxy)-2,2'-bipyrimidin-4-yl)benzenesulfonamide (17a)

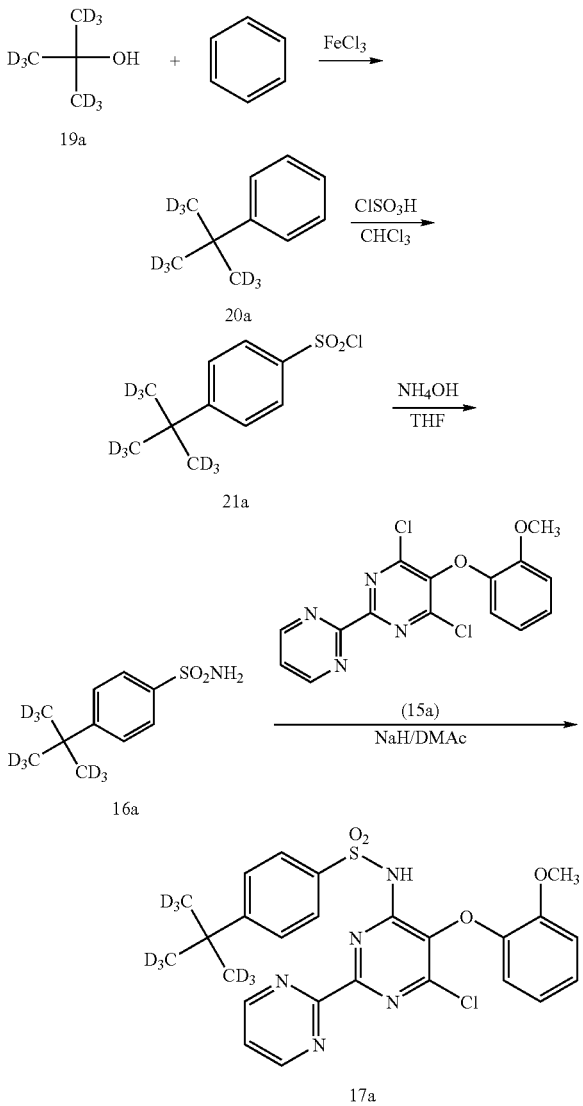

Scheme 5. Preparation of Intermediate 17a.

Step 1. (tent-Butyl-d$_9$)-benzene (20a). A solution of d$_9$-tert-butanol, 19a (25.0 g, 0.3012 mol, 1.0 equiv) in benzene (20 mL) was added over 0.25 hour to a suspension of iron(III) chloride (48.8 g, 0.3012 mol, 1.0 equiv) in benzene (175 mL, 1.9615 mol, 6.5 equiv). Mild cooling was used to maintain the reaction temperature at 22-27° C. during the addition (benzene (5 mL) was used to rinse the addition funnel). The suspension was stirred at room temperature for 7.5 hours then diluted with hexanes (200 mL). The mixture was filtered through a pad of silica gel (0.5 in) topped with Celite (0.5 in), washing the pad with hexanes (700 mL). The filtrate was concentrated under reduced pressure (bath temperature about 20° C.) to a yellow liquid. The crude product was distilled to give 19.8 g (46%) of (tert-butyl-$d_9$)-benzene, 20a as a colorless liquid, by 55-60° C., 35-37 Torr).

Step 2. 4-(tert-Butyl-$d_9$)-benzene-1-sulfonyl chloride (21a). A solution of (tert-butyl-$d_9$)-benzene, 20a (19.3 g, 0.135 mol, 1.0 equiv) in chloroform (250 mL) was cooled to −5° C. in an ice/brine bath. Chlorosulfonic acid (44.1 g, 25 mL, 0.377 mol, 2.8 equiv) was added dropwise over 0.75 hour, maintaining the reaction temperature at −5° C.±1° C. The ice/brine bath was replaced with an ice/water bath and the mixture was stirred at 0-2° C. for 1 hour, then allowed to warm to room temperature and stirred 1 hour. The turbid mixture was poured cautiously onto ice (600 mL). The biphasic mixture was diluted with dichloromethane (200 mL). The organic phase was washed with water (500 mL), brine (2×500 mL), dried ($Na_2SO_4$), filtered and the filtrate concentrated under reduced pressure to an oily solid. The oily solid was placed under high vacuum for 1 hour to give 26.1 g (80%) of crude 4-(tert-butyl-$d_9$)-benzene-1-sulfonyl chloride, 21a. The crude product was used without further purification.

Step 3. 4-(tert-Butyl-$d_9$)-benzenesulfonamide (16a) A mixture of about 15N ammonium hydroxide (24.6 mL, 0.3703 mol, 3.5 equiv) and tetrahydrofuran (200 mL) was cooled to about 2° C. and a solution of crude 4-(tert-butyl-$d_9$)-benzene-1-sulfonyl chloride, 21a (25.5 g, 0.1058 mol, 1.0 equiv) in tetrahydrofuran (200 mL) was added dropwise over 0.75 hour at 2-5° C. The mixture (some solids coating sides of flask) was allowed to warm to room temperature and stirred 0.5 hour. Water (about 50 mL) was added to dissolve solids and the mixture was concentrated under reduced pressure to remove the bulk of the tetrahydrofuran. The residual oily mixture was partitioned between ethyl acetate (500 mL) and 1N hydrochloric acid (100 mL). The organic phase was washed with brine (100 mL), dried ($Na_2SO_4$), filtered and the filtrate concentrated under reduced pressure to a white solid, crude weight 25.9 g. TLC (30% ethyl acetate/heptanes): product ($R_f$=0.47) and 3 minor impurities ($R_f$=0.73, $R_f$=0.66, $R_f$=0.54). The crude product was absorbed onto silica gel using dichloromethane and dry-loaded on a column of silica gel (250 g) packed in toluene. The column was eluted with toluene (1.5 L), 10% ethyl acetate/toluene (2 L) and 25% ethyl acetate/toluene (1 L). The one mixed fraction was purified a second time by silica gel chromatography (150 g), eluting with a gradient of 0-30% ethyl acetate/heptanes. Product fractions from both columns were concentrated under reduced pressure to a white solid that was triturated with heptanes (150 mL), filtered and dried to give 21.9 g (93%) of 4-(tert-butyl-$d_9$)-benzenesulfonamide, 16a. $^1$H-NMR (300 MHz, CDCl$_3$): δ 4.93 (s, 2H), 7.52 (d, J=8.2, 2H), 7.86 (d, J=8.7, 2H). HPLC (method: 20 mm C18-RP column—gradient method 2-95% ACN+0.1% formic acid in 3.3 min with 1.7 min hold at 95% ACN; Wavelength: 254 nm): retention time=3.10 min. MS (M+H): 223.2, 206.1.

Step 4. 4-(tert-Butyl-$d_9$)-N-(6-chloro-5-(2-methoxyphenoxy)-2,2'-bipyrimidin-4-yl)benzenesulfonamide (17a) 60% Sodium hydride (0.97 g, 24.2 mmol, 2.2 equiv) was suspended in N,N'dimethylacetamide (50 mL) and the mixture was cooled in an ice-bath. 4-(tert-Butyl-$d_9$)-benzenesulfonamide, 16a (2.44 g, 11 mmol, 1.1 equiv) was added portionwise as a solid, maintaining the reaction temperature below 3° C. The white suspension was allowed to warm to room temperature over 0.75 hour, then cooled to approximately 5° C. 4,6-Dichloro-5-(2-methoxyphenoxy)-2,2-bipyrimidine, 15a [prepared by the method described in Bioorg. & Med. Chem., 2001, 9: 2955] (3.49 g, 10 mmol, 1.0 equiv) was added as a solid. The reaction mixture developed a yellow color but no exotherm was observed. The mixture was stirred at 2-5° C. for 0.25 hour (slow $H_2$ evolution), then was allowed to warm to room temperature and was stirred 3.5 hours (the rate of $H_2$ evolution increased as the mixture warmed, and the color of the mixture deepened to yellow-orange). The suspension was poured slowly into ice-water (200 mL) and the yellow suspension was adjusted to pH 1-2 with 1N hydrochloric acid. The yellow solid was filtered, washed with water (300 mL), dried on the filter for 1.5 hours, then dried overnight in a vacuum oven at 40-50° C. The crude product was dissolved in a minimum amount of dichloromethane containing a few mL of methanol and was absorbed onto silica gel. The absorbed material was dry-loaded onto a column of silica gel (65 g) packed in dichloromethane. The column was eluted with a gradient of 0-5% methanol/dichloromethane (slow elution). Clean product fractions were concentrated under reduced pressure to give a yellow foamy solid. The foamy solid was triturated with ethyl acetate (about 50 mL) to give a suspension. The suspension was concentrated to near dryness and diluted with 1:1 ethyl acetate/heptanes (150 mL). The solid was filtered, washed with 1:1 ethyl acetate/heptanes (25 mL) and dried to give 3.51 g (66%) of 4-$d_9$-tert-butyl-N-(6-chloro-5-(2-methoxyphenoxy)-2,2'-bipyrimidin-4-yl)benzenesulfonamide, 17a as a light-yellow solid. $^1$H-NMR (300 MHz, DMSO-$d_6$): δ 3.78 (s, 3H), 6.59 (bs, 1H), 6.81 (t, J=7.6, 1H), 7.02 (t, J=7.6, 1H), 7.09 (d, J=7.6, 1H), 7.42 (bs, 2H), 7.66 (t, J=4.7, 1H), 8.02 (bs, 2H), 9.05 (d, J=4.1, 2H). HPLC (method: 150 mm C18-RP column—gradient method 5-95% ACN; Wavelength: 254 nm): retention time=3.85 min. MS (M+H): 535.1.

Example 2

Synthesis of 4-(tert-Butyl-$d_9$)-N-(6-(2-hydroxyethoxy)-5-(2-methoxyphenoxy)-2,2'-bipyrimidin-4-yl)benzenesulfonamide (Compound 102)

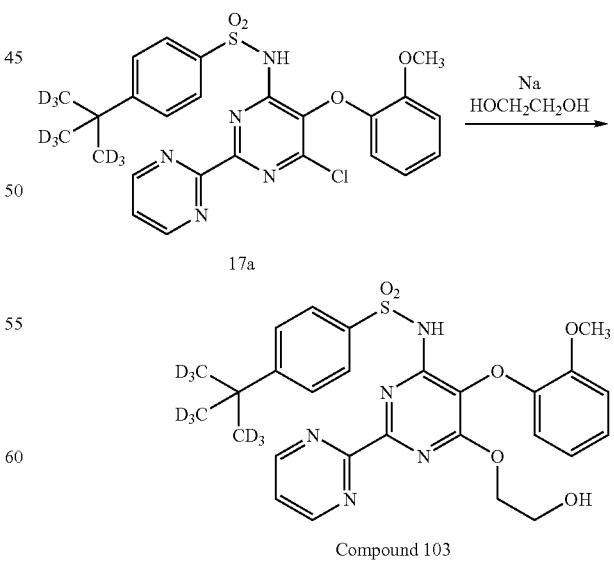

Scheme 6. Preparation of Compound 103.

Compound 103

4-(tert-Butyl-$d_9$)-N-(6-(-2-hydroxyethoxy)-5-(2-methoxyphenoxy)-2,2'-bipyrimidin-4-yl)benzenesulfonamide (Compound 103). Metallic sodium (0.14 g, 6.0 mmol, 3.0 equiv) was added to ethylene glycol (10 mL) and the mixture was heated at approximately 45° C. until all sodium dissolved. The clear solution was cooled to 30° C. and crude 17a (1.07 g, 2.0 mmol, 1.0 equiv) was added in one portion. The suspension was heated to approximately 95° C. A clear pale yellow solution formed after approximately 0.5 hour. The mixture was heated at approximately 95° C. for 3 hours, cooled to room temperature and stirred overnight. The mixture was poured into water (250 mL) and the light solution was acidified to pH 1-2 with 1N hydrochloric acid. The pale yellow suspension was stirred 10 minutes then allowed to stand for 10 minutes. The solid was filtered, washed well with water (100 mL), dried on the filter for 1.5 hours, then dried in a vacuum oven at 50-60° C. overnight. Recrystallization of the crude solid (1.00 g) from ethanol/water gave material of only 96.7% purity by HPLC. This solid and that recovered from the mother liquor were combined, dissolved in dichloromethane and adsorbed onto silica gel. The adsorbed material was dry-loaded onto a column of silica gel (25 g) packed in 75% ethyl acetate/heptanes. The column was eluted with 75% ethyl acetate/heptanes (400 mL), 100 ethyl acetate (500 mL), 2% methanol/ethyl acetate (800 mL) followed by 3% methanol/ethyl acetate. Product-containing fractions were concentrated under reduced pressure to a foamy oil. The foamy oil was dissolved in hot ethanol (10 mL), water (10 mL) was added dropwise and the mixture was allowed to cool to room temperature. Solids began to slowly form after approximately 2 hours. The suspension was stirred overnight. The solids were filtered, washed with cold 50% ethanol/water (5 mL) and dried. The solids were further dried in a vacuum oven at approximately 50° C. for 8 hours to give 0.57 g (51%) of Compound 103 as a pale yellow solid, mp 144.5-146.6° C. $^1$H-NMR (300 MHz, CDCl$_3$): δ 3.85-3.87 (m, 2H), 3.95 (s, 3H), 4.58-4.60 (m, 2H), 4.88 (bs, 1H), 6.85-6.90 (m, 1H), 6.98-7.16 (m, 3H), 7.40-7.44 (m, 3H), 8.40 (d, J=8.5, 2H), 8.75-8.78 (m, 1H), 9.01 (d, J=5.0, 2H). $^{13}$C-NMR (75 MHz, DMSO-d$_6$): δ 34.47, 56.00, 62.69, 72.10, 77.24, 112.42, 119.06, 121.20, 121.30, 124.62, 125.37, 129.46, 136.01, 145.53, 149.66, 151.73, 155.22, 157.26, 157.73, 161.19, 161.40. HPLC (method: 20 mm C18-RP column—gradient method 2-95% ACN+0.1% formic acid in 3.3 min with 1.7 min hold at 95% ACN; Wavelength: 254 nm): retention time: 3.56 min; 99.3% purity. MS (M+H): 561.3. Elemental Analysis ($C_{27}H_{20}D_9N_5O_6S$): Calculated: C=57.85, H=5.21, N=12.49, S=5.72. Found: C=57.63, H=5.19, N=12.46, S=5.74.

Example 3

Synthesis of 4-tert-Butyl-N-(6-(2-hydroxyethoxy)-5-(2-(methoxy-d$_3$)-phenoxy)-2,2'-bipyrimidin-4-yl)benzenesulfonamide (Compound 102)

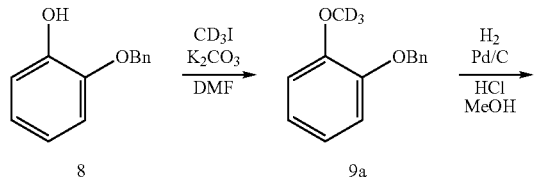

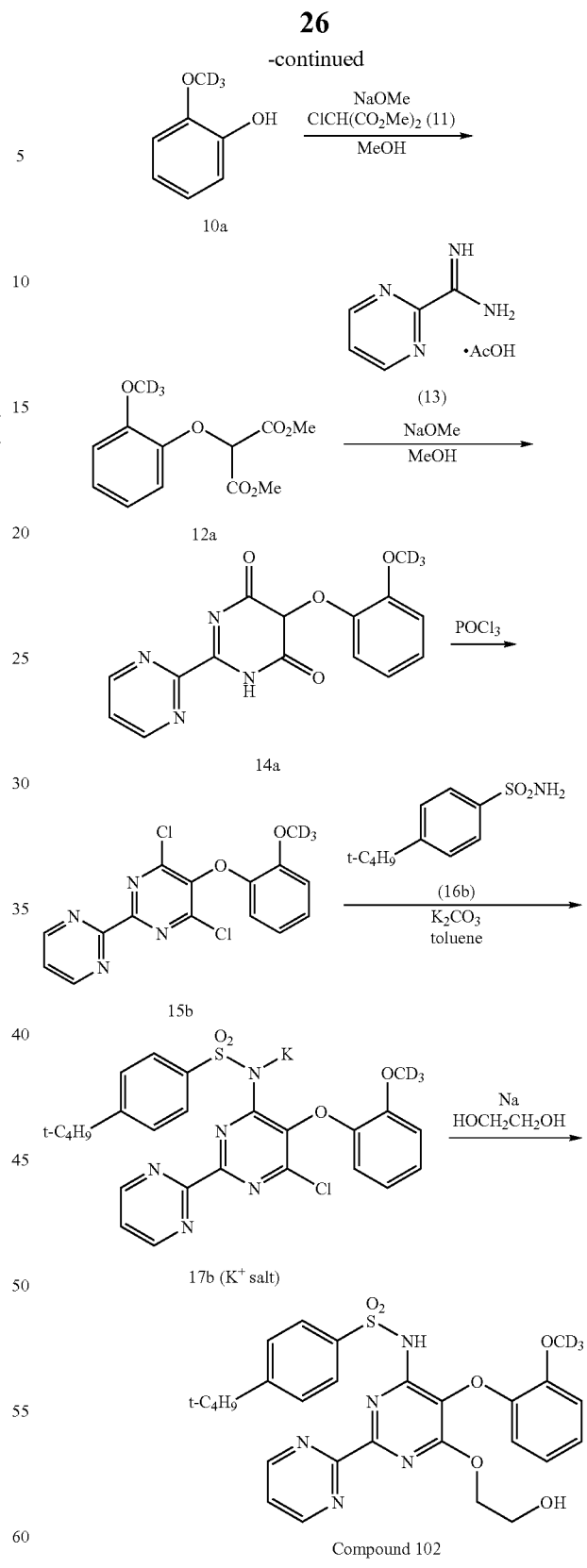

Step 1. 1-(Benzyloxy)-2-(methoxy-d$_3$)benzene (9a). Powdered potassium carbonate (69.0 g, 0.5 mol, 2.0 equiv) was added to a solution of 2-benzyloxyphenol (50 g, 0.25 mol, 1.0 equiv) in N,N'dimethylformamide (500 mL) with formation of a gray suspension. Iodomethane-d$_3$ (Isotec, 99.5 atom % D, 50 g, 0.3448 mol, 1.38 equiv) was added. The reaction temperature increased from 22° C. to 25° C. over 10 minutes, holding at 25° C. for 0.5 hour before dropping. The reaction mixture was stirred at room temperature for 1 hour, then heated at approximately 45° C. for 3 hours. The brown/tan suspension was cooled to room temperature and poured into water (1.5 L) giving an oil that crystallized. The aqueous mixture was extracted with 3:2 ethyl acetate/heptanes (1.25 L). The organic phase was diluted with heptanes (250 mL) and washed with water (4×500 mL), brine (500 mL), dried over sodium sulfate, filtered and the solvent removed under reduced pressure. The light yellow-brown oil was seeded to induce crystallization to give 54.6 g (approximately 100%) of 1-(benzyloxy)-2-$d_3$-methoxybenzene as a yellow-brown solid that was used without further purification.

Step 2. 2-(Methoxy-$d_3$)phenol (10a). 20% Palladium on carbon (approximately 55% water; 2.7 g) was added to a mixture of 1-(benzyloxy)-2-$d_3$-methoxybenzene (54.0 g, 0.2488 mol), methanol (900 mL) and 2N hydrochloric acid (30 mL). The mixture was hydrogenated at approximately 40 psi $H_2$ for 1 hour after uptake of $H_2$ ceased. The mixture was filtered through Celite, washing the Celite pad with methanol (500 mL). The filtrate was concentrated under reduced pressure. The oily residue was dissolved in dichloromethane and the organic solution washed with saturated brine (200 mL). The aqueous phase was back-extracted with dichloromethane (200 mL). The combined organic solution was dried over sodium sulfate, filtered and the solvent removed under reduced pressure to give 30.6 g (97%) of 2-$d_3$-methoxyphenol as a yellow-brown oil that was used without further purification.

Step 3. Dimethyl 2-(2-(Methoxy-$d_3$)-phenoxy)malonate (12a). A solution of 2-(methoxy-$d_3$)phenol, 10a (30.6 g, 0.2409 mol, 1.00 equiv) in methanol (200 mL) was cooled to 10° C. and a 25 wt % solution of sodium methoxide in methanol (52.0 g, 55 mL, 0.2409 mol, 1.00 equiv) was added slowly using methanol (100 mL) to rinse the graduated cylinder. A dark brown color developed and the reaction temperature increased from 10° C. to 19° C. The reaction mixture was stirred 10 min before the addition of dimethyl chloromalonate, 11 (44.4 g, 34 mL, 0.2674 mol, 1.11 equiv). The mixture was stirred 20 minutes during which time a light suspension formed. The mixture was heated to approximately 45° C. and held at this temperature for 6.25 hours. The mixture was cooled to room temperature and stirred overnight. The resulting brownish light suspension was concentrated under reduced pressure to remove methanol. The residual oily solid was partitioned between water (500 mL) and 1:1 toluene/heptanes (1 L). The organic phase was washed with 1% sodium hydroxide (500 mL), water (500 mL), brine (300 mL), dried over sodium sulfate, filtered and the solvent removed under reduced pressure to give 42.2 g (68%) of crude 12a as a pale yellow oil that was used without further purification.

Step 4. 5-(2-(Methoxy-$d_3$)phenoxy)-2-(pyrimidin-2-yl)pyrimidine-4.6(1H,5H)-dione (14a). 25 wt % Sodium methoxide in methanol (60.0 g, 63 mL, 278.0 mmol, 3.125 equiv) was added to methanol (600 mL). Pyrimidine-2-carboximidamide acetate, 13 (16.2 g, 89.0 mmol, 1.0 equiv; prepared from 2-cyanopyrimidine as described in Japanese Patent Application 2000344755A) was added and the orange solution stirred 10 minutes. Crude 14a (22.9 g, 89 mmol, 1.0 equiv) was added and the mixture heated to reflux. Upon heating the mixture developed a dark brown color which grew lighter once the reaction mixture reached reflux. The mixture was heated at reflux for 22 hours. The yellow-brown suspension was cooled to room temperature, concentrated under reduced pressure to near dryness and the residue was dissolved in water (350 mL). The dark green solution was cooled in an ice bath and acidified to pH 1-2 with 3N hydrochloric acid. The resulting suspension was stirred at room temperature for 0.25 hour then filtered. The solid was washed with water (250 mL) and dried on the filter for 0.25 hour. The tan solid was washed with 1:1 ethanol/heptanes (150 mL) followed by MTBE (150 mL) and dried to give 18.2 g (65%) of 14a that was used without further purification.

Step 5. 4,6-Dichloro-5-(2-(methoxy-$d_3$)phenoxy)-2,2'-bipyrimidine (15b). Intermediate 14a (14.9 g, 47.3 mmol, 1.0 equiv) was added portionwise to phosphorous oxychloride (72.8 g, 44 mL, 473 mmol, 10.0 equiv) with mild cooling to keep the reaction temperature below 30° C. The thick yellow-orange slurry was stirred 5 minutes before the dropwise addition (via syringe) of 2,4,6-trimethylpyridine (5.7 g, 5.9 mL, 47.3 mmol, 1.0 equiv), maintaining the reaction temperature below 25° C. during the exothermic addition. The reaction mixture was warmed slowly to reflux. A yellow-orange solution formed on heating which darkened to brown at reflux. After heating at reflux for 6 hours, the reaction mixture was cooled to room temperature and stirred overnight. The mixture was poured slowly into ice water (500 mL) with stirring. Ice was added periodically to temper the exothermic hydrolysis. The resulting suspension was stirred 10 minutes then extracted with dichloromethane (1×500 mL, 1×200 mL). The combined organic solution was washed with water (500 mL) and brine (500 mL). The organic phase was stirred 0.25 hour with sodium sulfate and charcoal (1.5 g). The mixture was filtered through a Celite pad (¼ inch) topped with silica gel (¼ inch). The filtrate was concentrated under reduced pressure to near dryness. The solid was triturated with 1:1 toluene/heptanes (120 mL) and the mixture concentrated to dryness. The solid was slurried in heptanes, filtered and dried to give 11.3 g (68%) of 15b as a white solid.

Step 6. Potassium (4-tert-Butylphenylsulfony)(6-chloro-5-(2-(methoxy-$d_3$)phenoxy)-2,2'-bipyrimidin-2-yl)amide (17b ($K^+$ salt)). A suspension of 15b (3.52 g, 10 mmol, 1.0 equiv), 16b (2.13 g, 10 mmol, 1.0 equiv; commercially-available), powdered potassium carbonate (1.66 g, 12 mmol, 1.2 equiv) and benzyltriethylammonium chloride (0.02 g) in toluene (150 mL) was heated at reflux for 22 hours with removal of water via a Dean-Stark trap. The mixture was cooled to room temperature, concentrated under reduced pressure to a small volume and the mixture was diluted with 1:1 toluene/ethyl acetate (50 mL). The solids were filtered, washed with 1:1 toluene/ethyl acetate (25 mL), dried under $N_2$ for 3 hours then in a vacuum oven for 2 hours at 50-55° C. to give 6.23 g (118%) of crude 17b ($K^+$ salt) as an off-white powder.

Step 7. 4-tert-Butyl-N-(6-(-2-hydroxyethoxy)-5-(2-(methoxy-$d_3$)phenoxy)-2,2'-bipyrimidin-4-yl)benzenesulfonamide (Compound 102). Metallic sodium (0.26 g, 11.34 mmol, 3.0 equiv) was added to ethylene glycol (15 mL) and the mixture was heated at 45-48° C. until all sodium dissolved. To the clear solution crude 17b ($K^+$ salt) (2.00 g, 3.78 mmol, 1.0 equiv) was added in one portion. The suspension was heated at 95-98° C. for 3.5 hours. A clear pale yellow solution formed after approximately 1 hour. The mixture was cooled to room temperature and stirred overnight. The mixture was poured into water (250 mL). The suspension was acidified with 1N hydrochloric acid (25 mL). The pale yellow suspension was stirred 10 minutes then allowed to stand for 15 minutes. The solid was filtered, washed with water (100 mL) and dried on the filter for 4 hours. The solid was dissolved in ethanol (15 mL) and water (15 mL) was added slowly and the mixture was heated to approximately 50° C. The solution was allowed to cool slowly to room temperature. A oil began forming. Ethanol (3 mL) was added dropwise and the mixture heated to near reflux. The solution was allowed to cool slowly to room temperature within the heating mantle and was stirred overnight. The resulting solids were filtered, washed with cold 50% ethanol/water (24 mL) and dried to give 0.98 g (47%) of Compound 102 as a pale yellow solid, mp 138.8-139.7° C. $^1$H-NMR (300 MHz, CDCl$_3$): δ 1.29 (s, 9H), 3.85-3.87 (m, 2H), 4.57-4.60 (m, 2H), 6.87-6.97 (m, 1H), 6.99-7.12 (m, 3H), 7.40-7.45 (m, 3H), 8.44 (d, J=8.5, 2H), 8.85 (bs, 1H), 9.01 (d, J=5.0, 2H). $^{13}$C-NMR (75 MHz, DMSO-d$_6$): δ 31.03, 35.14, 62.66, 72.06, 77.25, 112.39, 119.05, 121.17, 121.31, 124.61, 125.37, 129.45, 136.03, 145.52, 149.63, 151.74, 155.22, 157.22, 157.73, 161.20, 161.38. HPLC (method: 20 mm C18-RP column—gradient method 2-95% ACN+0.1% formic acid in 3.3 min with 1.7 min hold at 95% ACN; Wavelength: 254 nm): retention time: 3.54 min; 99.8% purity. MS (M+H): 555.3. Elemental Analysis (C$_{27}$H$_{26}$D$_3$N$_5$O$_6$S): Calculated: C=58.47, H=5.27, N=12.63, S=5.78. Found: C=57.94, H=5.15, N=12.44, S=5.92.

Example 4

Synthesis of 4-(tert-Butyl-d$_9$)-N-(6-(2-hydroxyethoxy)-5-(2-(methoxy-d$_3$)-phenoxy)-2,2'-bipyrimidin-4-yl)benzenesulfonamide (Compound 101)

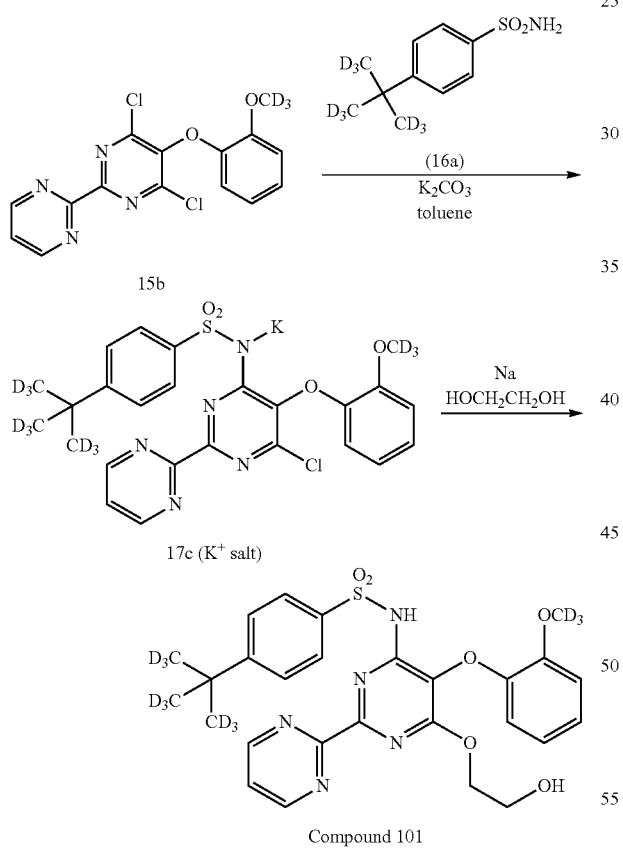

Step 1. Potassium (4-(tert-Butyl-d$_9$)-phenylsulfony)(6-chloro-5-(2-(methoxy-4)-phenoxy)-2,2'-bipyrimidin-2-yl) amide (17c (K$^+$ salt)). A suspension of 15b (3.52 g, 10 mmol, 1.0 equiv, see Example 3, Step 5 for preparation), 16a (2.22 g, 10 mmol, 1.0 equiv, see Example 1, Step 3 for preparation), powdered potassium carbonate (1.66 g, 12 mmol, 1.2 equiv) and benzyltriethylammonium chloride (0.02 g) in toluene (150 mL) was heated to reflux for 8 hours with removal of water via a Dean-Stark trap. The suspension was cooled to room temperature and stirred overnight. The reaction mixture was concentrated to approximately ⅓ volume and diluted with ethyl acetate (50 mL). The solids were filtered, washed with 1:1 toluene/ethyl acetate (50 mL), dried under N$_2$ for 0.75 hour then in a vacuum oven at approximately 50° C. for 6 hours to give 6.17 g (107%) of crude 17c (K$^+$ salt) as an off-white solid that was used without further purification.

Step 2. 4-(tert-Butyl-d$_9$)-N-(6-(-2-hydroxyethoxy)-5-(2-(methoxy-d$_3$)-phenoxy)-2,2'-bipyrimidin-4-yl)benzenesulfonamide (Compound 101). Metallic sodium (0.24 g, 10.42 mmol, 3.0 equiv) was added to ethylene glycol (15 mL) and the mixture heated at approximately 45° C. until all sodium dissolved. To the clear solution, crude 17c (K$^+$ salt) (2.00 g, 3.47 mmol, 1.0 equiv) was added in one portion. The suspension was heated at approximately 95° C. for 6 hours. A clear pale yellow solution formed after approximately 1 hour. The mixture was cooled to room temperature and stirred overnight. The mixture was poured into water (150 mL). The suspension was acidified with 1N hydrochloric acid (20 mL). The pale yellow suspension was allowed to stand for 10 minutes. The particle size of the suspension was too fine for filtration so the mixture was extracted with ethyl acetate (150 mL). The organic phase was washed with water (2×50 mL), brine (50 mL), dried over sodium sulfate, filtered and the solvent removed under reduced pressure to give a yellow foam. Residual ethyl acetate was coevaporated with ethanol (2×40 mL) to give a yellow gummy foam. The crude product was dissolved in ethanol (15 mL), water (15 mL) was added slowly, and the mixture was heated to reflux. The solution was allowed to cool slowly to room temperature and was stirred overnight. The solids were filtered, washed with cold 50% ethanol/water (10 mL) dried on the filter for 2 hours then in a vacuum oven at approximately 45-50° C. for 4 hours to give 1.05 g (54%) of Compound 101 as a pale yellow solid, mp 138.7-139.5° C. $^1$H-NMR (300 MHz, CDCl$_3$): δ 3.84-3.88 (m, 2H), 4.58-4.60 (m, 2H), 4.92 (t, J=6.4, 1H), 6.84-6.90 (m, 1H), 6.97-7.15 (m, 3H), 7.40-7.44 (m, 3H), 8.44 (d, J=8.8, 2H), 8.81 (bs, 1H), 9.01 (d, J=5.0, 2H). $^{13}$C-NMR (75 MHz, DMSO-d$_6$): δ 34.72, 62.97, 72.42, 77.46, 112.64, 119.34, 121.42, 121.54, 124.88, 125.61, 129.70, 136.23, 145.76, 149.90, 151.98, 155.46, 157.50, 157.97, 161.42, 161.64. HPLC (method: 20 mm C18-RP column—gradient method 2-95% ACN+0.1% formic acid in 3.3 min with 1.7 min hold at 95% ACN; Wavelength: 254 nm): retention time: 3.53 min; 99.5% purity. MS (M+H): 564.3. Elemental Analysis (C$_{27}$H$_{17}$D$_{12}$N$_5$O$_6$S): Calculated: C=57.54, H=5.19, N=12.43, S=5.69. Found: C=57.11, H=5.07, N=12.24, S=5.70.

Example 5

Synthesis of 2-tert-Butoxy-2,2-d$_2$-ethanol (Intermediate 18a)

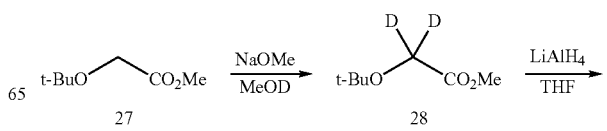

31
-continued

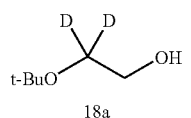

18a

Step 1. Methyl 2-tent-butoxy-2,2-$d_2$-acetate (28). Metallic sodium (0.40 g, 0.0174 mol, 11 mol %) was dissolved in methanol-d1 (Aldrich, 99.5 atom % D, 25 mL) and the solution was added to a solution of crude methyl 2-tert-butoxyacetate, 27 (22.5 g, 0.154 mol, see Denmark, S. et al., JOC, 2008, 73(12): 4582-4595) in methanol-d1 (240 mL). The mixture was stirred at room temperature for 95 hours, then concentrated under reduced pressure (bath temperature 17-19° C.) to give a yellow oil. $^1$H NMR showed that the hydrogen/deuterium exchange was approximately 80% complete. The oil was dissolved in fresh methanol-d1 (140 mL) and the solution was stirred at room temperature over the weekend. The mixture was concentrated under reduced pressure (bath temperature 16-17° C.). The residual oily solid was partitioned between hexanes (250 mL) and a solution of 35% deuterium chloride solution in deuterium oxide (Aldrich, 99 atom % D, 0.5 mL) in deuterium oxide (Cambridge Isotopes, 99 atom % D, 10 mL). The organic phase was dried over sodium sulfate, filtered and the solvent removed under reduced pressure (bath temperature 16-17° C.) to give a pale yellow oil (approximately 17.0 g). $^1$H NMR showed that the hydrogen/deuterium exchange was approximately 94.5%. The oil was dissolved in methanol-d1 (150 mL) and a solution of metallic sodium (0.23 g) in methanol-d1 (10 mL) was added. The mixture was stirred at room temperature for 96 hours. Work-up as above gave a pale yellow oil (approximately 13 g). $^1$H NMR showed that the hydrogen/deuterium exchange was approximately 97%. The oil was subjected to a $4^{th}$ exchange cycle (0.19 g of sodium, 150 mL of methanol-d1) for 4 days. Work-up as above gave 10.6 of methyl 2-tert-butoxy-2,2-$d_2$-acetate, 28 as a pale yellow oil that was used without further purification. $^1$H NMR showed that the hydrogen/deuterium exchange was approximately 99%.

Step 2. 2-tent-Butoxy-2,2-$d_2$-ethanol (18a). A solution of methyl 2-tert-butoxy-2,2-$d_2$-acetate, 28 (7.76 g, 51.8 mmol, 1.0 equiv) in tetrahydrofuran (75 mL) was cooled to −20° C. and 1M lithium aluminum hydride in tetrahydrofuran (64 mL, 64 mmol, 1.23 equiv) was added via syringe, maintaining the reaction temperature at or below −10° C. A suspension formed during the addition, which then dissolved to give a clear solution. The reaction mixture was stirred at −20±5° C. for 1 hour, then allowed to warm to room temperature over 1.5 hours. The mixture was cooled in a ice bath and quenched by sequential dropwise addition of water (2.4 mL), 15% sodium hydroxide (2.4 mL) and water (7.2 mL) maintaining the reaction temperature at or below −10° C. The white suspension was allowed to warm to room temperature and was stirred 0.5 hour. The mixture was filtered, washing the solids with tetrahydrofuran (200 mL). The filtrate was concentrated under reduced pressure to give 5.24 g (84%) of 2-tert-butoxy-2,2-$d_2$-ethanol, 18a as a colorless oil. $^1$H NMR showed approximately 97.5-98% isotopic purity. The crude product was used without further purification.

32

Example 6

Synthesis of 4-tert-Butyl-N-(6-(2-hydroxy-2,2-$d_2$-ethoxy)-5-(2-methoxyphenoxy)-2,2'-bipyrimidin-4-yl)benzenesulfonamide (Compound 104)

Scheme 10. Preparation of Compound 104.

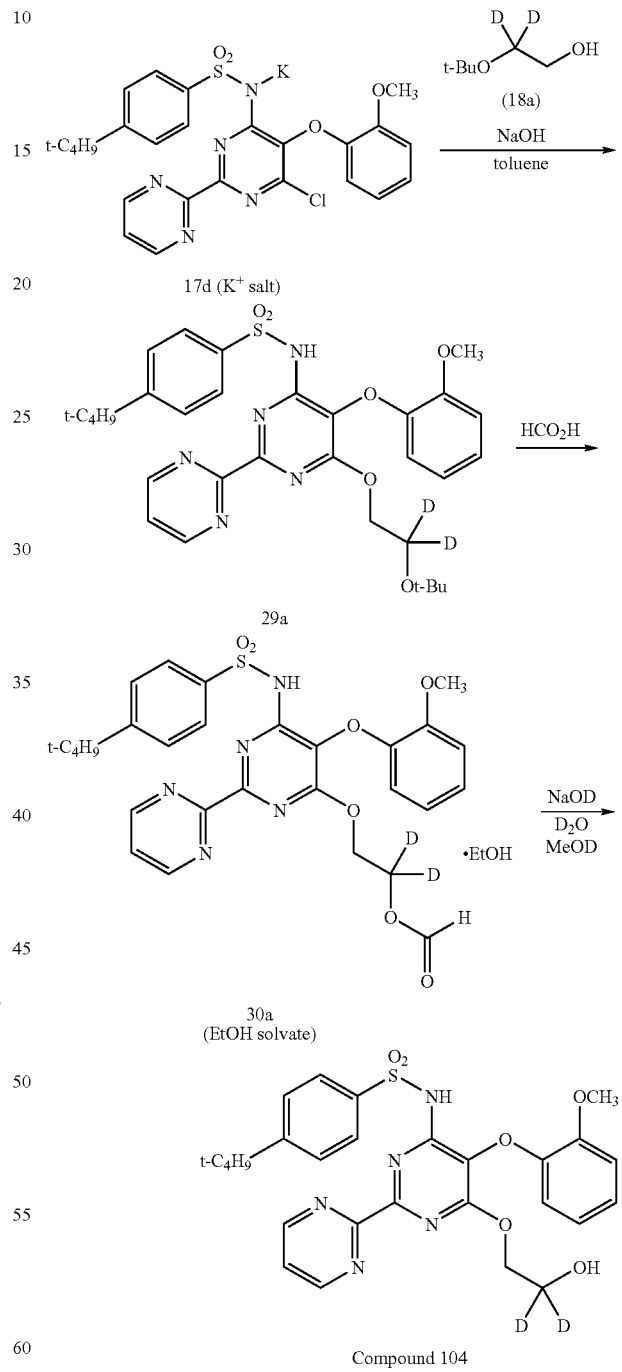

Step 1. N-(6-(2-tert-butoxy-2,2-$d_2$-ethoxy)-5-(2-methoxyphenoxy)-2,2'-bipyrimidin-4-$Y^1$)-4-tert-butylbenzenesulfonamide (29a). A mixture of 6N sodium hydroxide (1.7 mL, 10.2 mmol, 2.0 equiv) and toluene (150 mL) was heated to reflux with a Dean-Stark trap to remove water. The mixture was cooled to approximately 30° C., and a crude portion of known 17d (K+ salt) (2.87 g, 5.1 mmol, 1.0 equiv; see Harrington, P J. et al., Org. Proc. Res. Dev., 2002, 6(2): 120-124) and 2-tert-butoxy-2,2-$d_2$-ethanol, 18a (1.83 g, 15.25 mmol, 3.0 equiv, see Example 5) were added. The suspension was heated overnight at approximately 55° C. Benzyltriethylammonium chloride (0.11 g, 10 mol %) was added and the reaction mixture was heated an additional 24 hours at approximately 55° C. The yellow-green suspension was cooled to room temperature and diluted with ethyl acetate (100 mL). The mixture was washed with 0.5 N hydrochloric acid (50 mL), water (50 mL), brine (100 mL), dried over sodium sulfate, filtered and the solvent removed under reduced pressure to give a yellow viscous oil. The crude product was adsorbed onto silica gel using dichloromethane and dry-loaded onto a column of silica gel (100 g) packed in 75% ethyl acetate/heptanes. The column was eluted with 75% ethyl acetate/heptanes followed by 100% ethyl acetate. Product-containing fractions were concentrated under reduced pressure to near dryness. Residual ethyl acetate was coevaporated with toluene (2×50 mL) to afford 29a, 2.55 g of a yellow viscous oil, which was used in the following step without further purification.

Step 2. 2-(6-(4-tert-Butylphenylsulfonamido)-5-(2-methoxyphenoxy)-2,2'-bipyrimidin-4-yloxy)-1,1-$d_2$-ethyl formate (30a (EtOH solvate)). A mixture of 29a (2.55 g) and 96% formic acid (17 mL) was heated at 85-90° C. for 3 hours. The mixture was cooled to room temperature, diluted with toluene (50 mL) and concentrated under reduced pressure. Residual formic acid was coevaporated with toluene (2×50 mL). The residual oil was dissolved in ethanol (30 mL) and the mixture rotated on a rotary evaporator until crystallization was complete. The mixture was concentrated under reduced pressure to give 2.12 g of crude 30a EtOH solvate as a tan solid. The crude product was used without further purification.

Step 3. 4-tert-Butyl-N-(6-(2-hydroxy-2,2-$d_2$-ethoxy)-5-(2-methoxyphenoxy)-2,2'-bipyrimidin-4-yl)benzenesulfonamide (Compound 104). 40 wt % Sodium hydroxide-d in deuterium oxide (Aldrich, 99 atom % D, 1.00 g, 0.66 mL, 9.85 mmol, 3.0 equiv) was added to a suspension of 30a EtOH solvate (2.06 g, 3.28 mmol, 1.0 equiv) in methanol-d1 (Aldrich, 99.5 atom % D, 30 mL) and deuterium oxide (Cambridge Isotopes, 99 atom % D, 10 mL) with a clear yellow solution forming. The mixture was stirred at room temperature for 1 hour, then cooled in an ice bath and acidified to pH approximately 5 with concentrated hydrochloric acid. While cold, water (20 mL) was added drop-wise to the reaction mixture. Turbidity developed followed by formation of a yellow gum that was allowed to stand overnight. The partially solidified product was extracted into dichloromethane (75 mL). The organic solution was dried over sodium sulfate, filtered and the solvent removed under reduced pressure to give a yellow foamy gum. The gum was dissolved in ethanol (25 mL) and the solution heated to approximately 60° C. Water (15 mL) was added slowly drop-wise at 50-60° C. The faintly turbid mixture was allowed to cool to room temperature and stirred over a weekend. The solid was filtered, washed with cold 50% ethanol/water (12 mL) and dried to give 0.97 g (54%) of Compound 104 as a pale yellow solid, mp 142.3-144.4° C. The sample was further dried in a vacuum oven at approximately 45° C. for 6 hours. $^1$H-NMR (300 MHz, CDCl$_3$): δ 1.30 (s, 9H), 3.95 (s, 3H), 4.58 (s, 2H), 4.87 (s, 1H), 6.86-6.91 (m, 1H), 6.99-7.16 (m, 3H), 7.41-7.46 (m, 3H), 8.44 (d, J=8.5, 2H), 8.74 (bs, 1H), 9.01 (d, J=5.0, 2H). $^{13}$C-NMR (75 MHz, DMSO-d$_6$): δ 31.04, 35.15, 56.00, 72.08, 77.22, 112.42, 119.10, 121.21, 121.30, 124.64, 125.37, 129.47, 136.01, 145.53, 149.68, 151.73, 155.23, 157.24, 157.74, 161.18, 161.41. HPLC (method: 20 mm C18-RP column—gradient method 2-95% ACN+0.1% formic acid in 3.3 min with 1.7 min hold at 95% ACN; Wavelength: 254 nm): retention time: 3.53 min; 99.6% purity. MS (M+H): 554.1. Elemental Analysis (C$_{27}$H$_{27}$D$_2$N$_5$O$_6$S•H$_2$O): Calculated: C=57.64, H=5.37, N=12.45, S=5.70. Found: C=57.68, H=5.21, N=12.38, S=5.78.

Example 7

Synthesis of 4-(tert-Butyl-d$_9$)-N-(6-(2-hydroxy-2,2-d$_2$-ethoxy)-5-(2-(methoxy-d$_3$)phenoxy)-2,2'-bipyrimidin-4-yl)benzenesulfonamide (Compound 106)

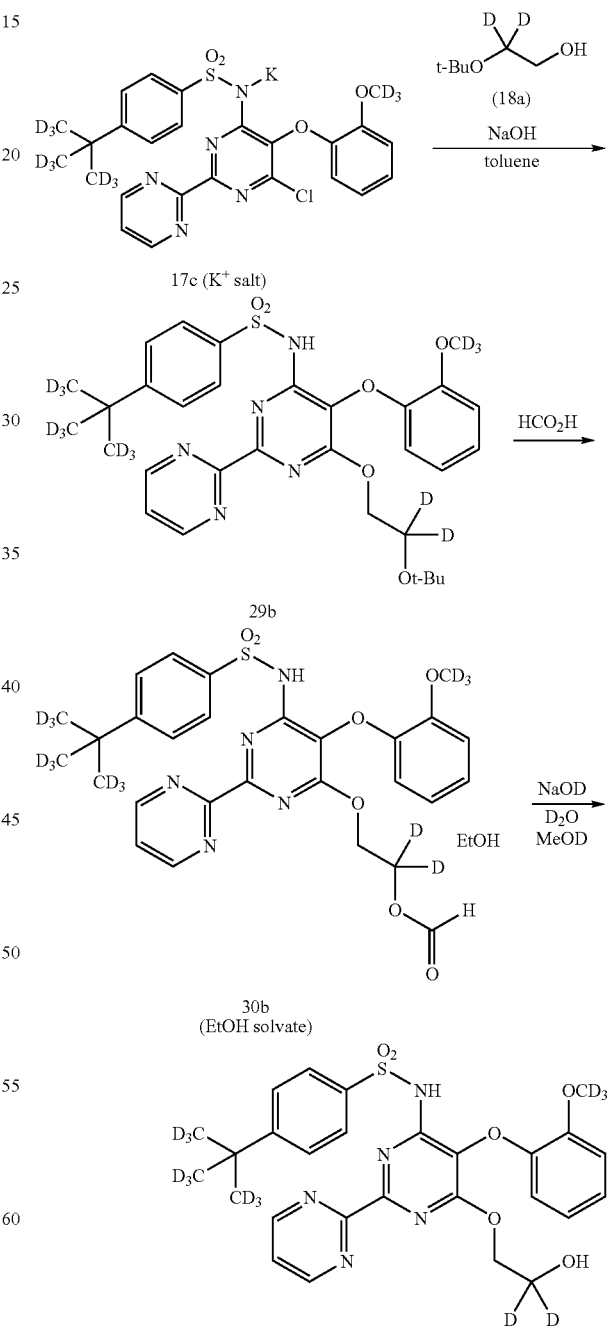

Scheme 11. Preparation of Compound 106.

Step 1. 4-(tert-Butyl-$d_9$)-N-(6-(-2-tert-butoxy-2,2-$d_2$-ethoxy)-5-(2-(methoxy-$d_3$)phenoxy)-2,2'-bipyrimidin-4-yl)benzenesulfonamide (29b). A mixture of 6N sodium hydroxide (1.7 mL, 10.0 mmol, 2.0 equiv) and toluene (150 mL) was heated to reflux with a Dean-Stark trap to remove water. The mixture was cooled to room temperature, crude 17c (K$^+$ salt) (2.88 g, 5.0 mmol, 1.0 equiv) and 2-tert-butoxy-2,2-$d_2$-ethanol, 18a (1.80 g, 15.0 mmol, 3.0 equiv) and benzyltriethylammonium chloride (0.11 g, 10 mol %) were added. The suspension was heated over a weekend at approximately 55° C. Benzyltriethylammonium chloride (0.11 g, 10 mol %) was added and the reaction mixture was heated an additional 24 hours at approximately 55° C. 6N Sodium hydroxide (0.85 mL) was added and the mixture heated at approximately 55° C. for an additional 3 days. The green suspension was cooled to room temperature, transferred to a separatory funnel and shaken with 1N hydrochloric acid (50 mL). The organic phase was washed with water (50 mL), brine (100 mL), dried over sodium sulfate, filtered and the solvent removed under reduced pressure to give a yellow viscous oil. The crude product was adsorbed onto silica gel using dichloromethane and dry-loaded onto a column of silica gel (100 g) packed in 50% ethyl acetate/heptanes. The column was eluted with 50% ethyl acetate/heptanes, 75% ethyl acetate/heptanes followed by 100% ethyl acetate. Product fractions were concentrated under reduced pressure to near dryness. Residual ethyl acetate was co-evaporated with toluene (2×50 mL) to give 2.20 g of 29b as a yellow gum.

Step 2. 4-(tert-Butyl-$d_9$)-N-(6-(-2-formyloxy-2,2-$d_2$-ethoxy)-5-(2-(methoxy-$d_3$)phenoxy)-2,2'-bipyrimidin-4-Y$^1$)benzenesulfonamide (30b (EtOH solvate)). A mixture of 29a (2.13 g) and 96% formic acid (20 mL) was heated at 85-90° C. for 4 hours. The mixture was cooled to room temperature, diluted with toluene (50 mL) and concentrated under reduced pressure. Residual formic acid was co-evaporated with toluene (50 mL). The residual oil was dissolved in ethanol (25 mL) and the solution was concentrated under reduced pressure. This process was repeated to effect crystallization of the solvate, but crystallization did not occur. The mixture was concentrated under reduced pressure to give 1.87 g of crude 30b EtOH solvate as a pale yellow foam.

Step 3. 4-(tert-Butyl-$d_9$)-N-(6-(2-hydroxy-2,2-$d_2$-ethoxy)-5-(2-(methoxy-$d_3$)phenoxy)-2,2'-bipyrimidin-4-yl)benzenesulfonamide (Compound 106). The EtOH solvate of 30b (1.64 g, 2.57 mmol, 1.0 equiv) was dissolved in methanol-d1 (Aldrich, 99.5 atom % D, 30 mL). Several minutes after dissolution, solids began precipitating. The suspension was diluted with deuterium oxide (Cambridge Isotopes, 99 atom % D, 10 mL) and 40 wt % sodium hydroxide-d in deuterium oxide (Aldrich, 99 atom % D, 0.79 g, 0.52 mL, 7.70 mmol, 3.0 equiv) was added drop-wise giving a pale yellow solution. The mixture was stirred at room temperature for 1 hour. The mixture was cooled in an ice/water bath and acidified to pH of approximately 3 with concentrated hydrochloric acid. Water (4 mL) was added drop-wise over 1 hour to the cold solution until faint turbidity persisted. The mixture was allowed to warm to room temperature with solids slowly forming. The mixture was stirred overnight, filtered, and the solids were washed with cold 50% ethanol/water. After drying for 1 hour, LCMS of the solid (1.11 g) showed purity was approximately 97.3%. The solid was dissolved in ethanol (25 mL) by warming to approximately 60° C., and water (15 mL) was added drop-wise at 55-60° C. The mixture was allowed to cool to room temperature and stirred. No solids precipitated. More water (approximately 5 mL) was added drop-wise and the mixture stirred overnight. Precipitated solids were filtered and washed with cold 50% ethanol/water (14 mL). The solids were dried on the filter for 1 hour then in a vacuum oven at approximately 50° C. overnight to give 0.43 g of Compound 106 as a pale yellow solid, mp 144.8-145.0° C. The mother liquor was concentrated to a yellow, tacky solid. The material was recrystallized from 50% ethanol/water (20 mL) to give an additional 0.41 g of Compound 106 as a as a pale yellow solid, mp 139.6-140.2° C. Total yield of Compound 106 was 0.83 g (57%). $^1$H-NMR (300 MHz, CDCl$_3$): δ 4.58 (s, 2H), 4.87, (s, 1H), 6.86-6.91 (m, 1H), 6.98-7.16 (m, 3H), 7.40-7.45 (m, 3H), 8.44 (d, J=8.8, 2H), 8.74 (bs, 1H), 9.01 (d, J=4.7, 2H). $^{13}$C-NMR (75 MHz, DMSO-$d_6$): δ 34.72, 62.97, 72.42, 77.46, 112.64, 119.34, 121.42, 121.54, 124.88, 125.61, 129.70, 136.23, 145.76, 149.90, 151.98, 155.46, 157.50, 157.97, 161.42, 161.64. HPLC (method: Waters Atlantis T3 2.1×50 mm 3 μm C18-RP column—gradient method 5-95% ACN+0.1% formic acid in 14 min (1.0 mL/min) with 4 min hold at 95% ACN; Wavelength: 254 nm): retention time: 7.56 min; 98.6% purity. MS (M+H): 566.4. Elemental Analysis ($C_{27}H_{15}D_{14}N_5O_6S•H_2O$): Calculated: C=56.44, H=5.26, N=12.19, S=5.58. Found: C=56.20, H=5.19, N=12.21, S=5.64.

Example 8

Evaluation of Metabolic Stability in CYP3A4 Supersomes

Materials: CYP3A4 Supersomes™ were obtained from BD Gentest. β-nicotinamide adenine dinucleotide phosphate, reduced form (NADPH), magnesium chloride (MgCl$_2$), and dimethyl sulfoxide (DMSO) were purchased from Sigma-Aldrich.

Determination of Metabolic Stability: 7.5 mM stock solutions of test compounds were prepared in DMSO. The 7.5 mM stock solutions were diluted to 50 μM in acetonitrile (ACN). The 1000 pmol/mL CYP3A4 supersomes were diluted to 50 pmol/mL in 0.1 M potassium phosphate buffer, pH 7.4, containing 3 mM MgCl$_2$. The diluted supersomes were added to wells of a 96-well deep-well polypropylene plate in triplicate. 10 μL of the 50 μM test compound was added to the supersomes and the mixture was pre-warmed for 10 minutes. Reactions were initiated by addition of pre-warmed NADPH solution. The final reaction volume was 0.5 mL and contained 40 pmol/mL CYP3A4 supersomes, 1 μM test compound, and 2 mM NADPH in 0.1 M potassium phosphate buffer, pH 7.4, and 3 mM MgCl$_2$. The reaction mixtures were incubated at 37° C. and 50 μL aliquots were removed at 0, 5, 10, 20, and 30 minutes and added to shallow-well 96-well plates which contained 50 μL of ice-cold ACN with internal standard to stop the reactions. The plates were stored at 4° C. for 20 minutes after which 100 μL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer.

Data analysis: The in vitro $t_{1/2}$s for test compounds were calculated from the slopes of the linear regression of % parent remaining (ln) vs incubation time relationship.

in vitro $t_{1/2}$=0.693/k k=−[slope of linear regression of % parent remaining(ln) vs incubation time]

Data analysis was performed using Microsoft Excel Software.

The results are shown in the FIGURE and Table 2, below.

TABLE 2

Calculated Half-Lives of Compounds of the Invention in CYP3A4 Supersomes.

| Compound | $t_{1/2}$ (minutes) | | | |
|---|---|---|---|---|
| | Experiment 1 | Experiment 2 | Ave $t_{1/2}$ (minutes) | % Difference* |
| Bosentan | 34.3 | 37.2 | 35.8 | — |
| Compound 103 | 35.9 | 40.5 | 38.2 | 6.7 |
| Compound 102 | 45.7 | 46.8 | 46.2 | 29.1 |
| Compound 104 | 30.9 | 32.4 | 31.6 | −11.7 |
| Compound 106 | 53.3 | 57.2 | 55.2 | 54.2 |
| Compound 101 | 41.0 | 41.3 | 41.2 | 15.1 |

*% Difference = [(deuterated species) − (nondeuterated species)](100)/(nondeuterated species)

Under the assay conditions tested, the in vitro tins for Compounds 101, 102 and 106 showed an approximate 15%, 29% and 54% increase, respectively, over non-deuterated bosentan.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

I claim:

1. A compound of the formula (I):

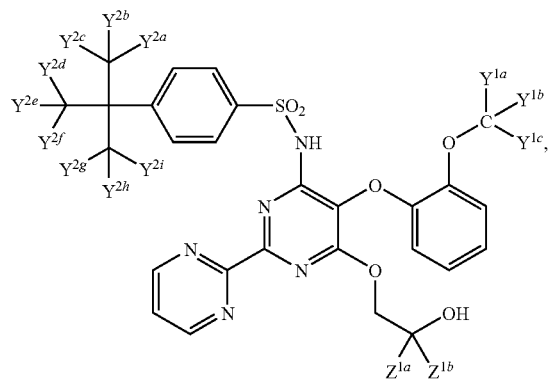

(I)

or a pharmaceutically acceptable salt thereof, wherein:
each Y is independently selected from hydrogen or deuterium, and $Y^{2a}$ is additionally selected from OH;
each Z is independently selected from hydrogen, deuterium, or fluorine; and
at least one Y or Z is deuterium.

2. The compound according to claim 1, wherein each $Y^1$ is the same.

3. The compound of claim 2 wherein each $Y^1$ is simultaneously deuterium.

4. The compound of claim 2 wherein each $Y^1$ is simultaneously hydrogen.

5. The compound according to claim 1, wherein $Y^{2b}$, $Y^{2c}$ $Y^{2d}$, $Y^{2e}$, $Y^{2f}$, $Y^{2g}$, $Y^{2h}$, and $Y^{2i}$ are the same.

6. The compound of claim 5, wherein $Y^{2a}$, $Y^{2b}$, $Y^{2c}$ $Y^{2d}$, $Y^{2e}$, $Y^{2f}$, $Y^{2g}$, $Y^{2h}$, and $Y^{2i}$ are the same.

7. The compound of claim 5, wherein $Y^{2a}$ is OH.

8. The compound of claim 5, wherein $Y^{2b}$, $Y^{2c}$ $Y^{2d}$, $Y^e$, $Y^{2f}$, $Y^{2g}$, $Y^{2h}$, and $Y^{2i}$ are simultaneously deuterium.

9. The compound of claim 5, wherein $Y^{2b}$, $Y^{2c}$ $Y^{2d}$, $Y^{2e}$, $Y^{2f}$, $Y^{2g}$, $Y^{2h}$, and $Y^{2i}$ are simultaneously hydrogen.

10. The compound according to claim 1, wherein $Z^{1a}$ and $Z^{1b}$ are simultaneously deuterium.

11. The compound according to claim 1, wherein $Z^{1a}$ and $Z^{1b}$ are simultaneously hydrogen.

12. The compound according to claim 1, wherein $Z^{1a}$ and $Z^{1b}$ are simultaneously fluorine.

13. The compound of claim 1, wherein the compound is selected from any one of the compounds below:

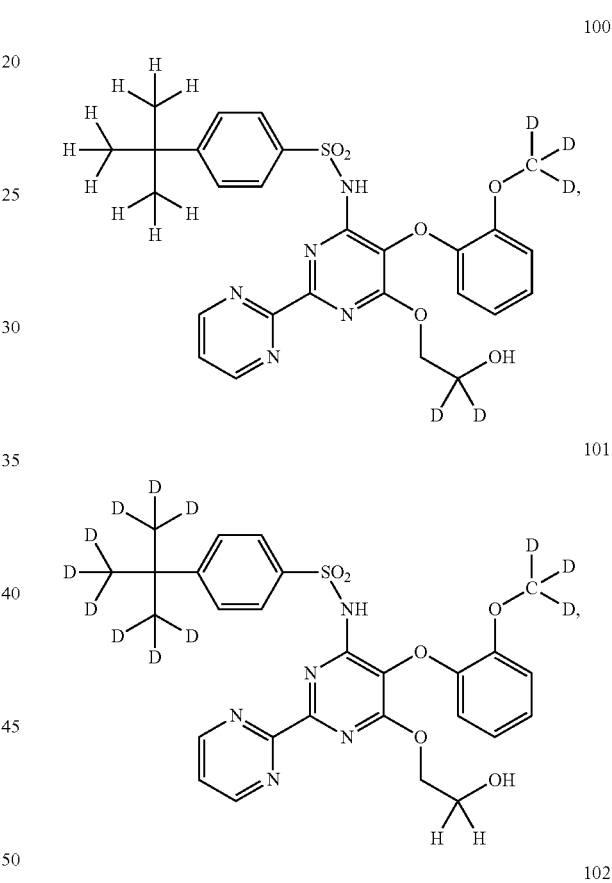

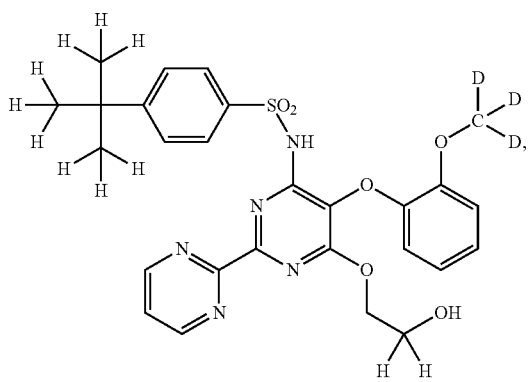

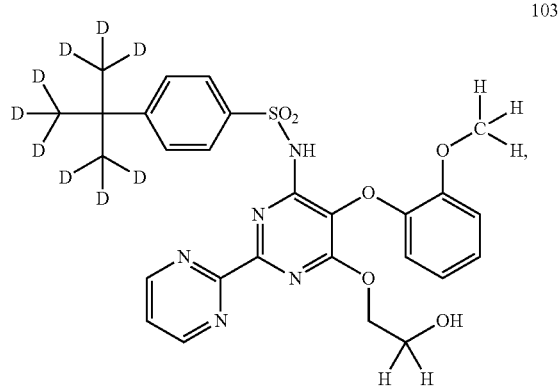
103
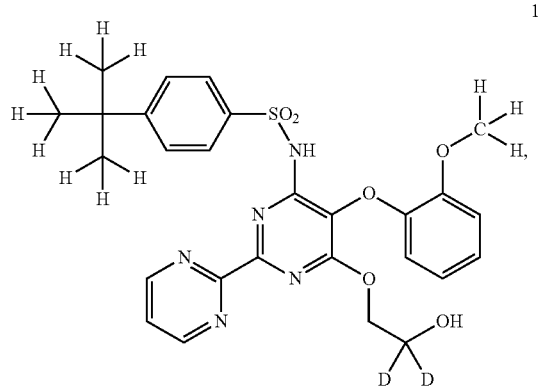
104
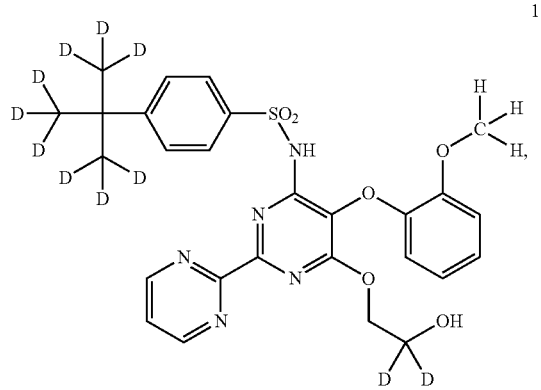
105
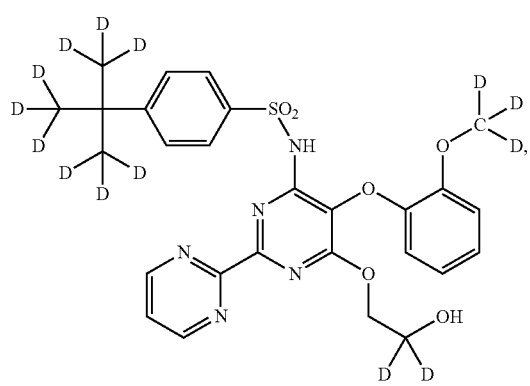
106
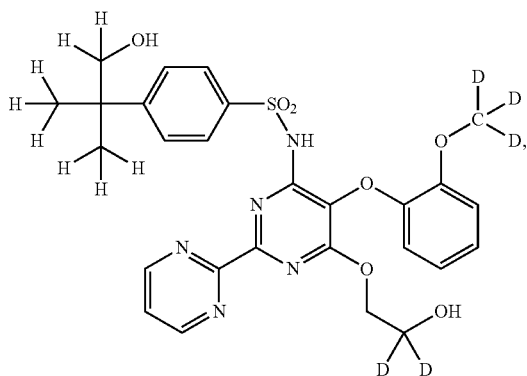
107
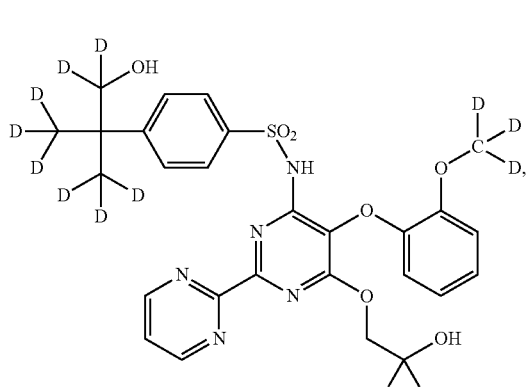
108
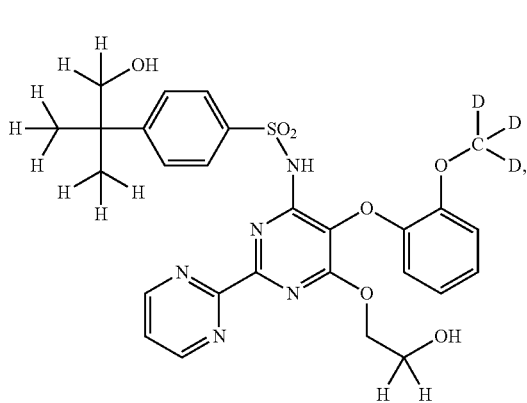
109
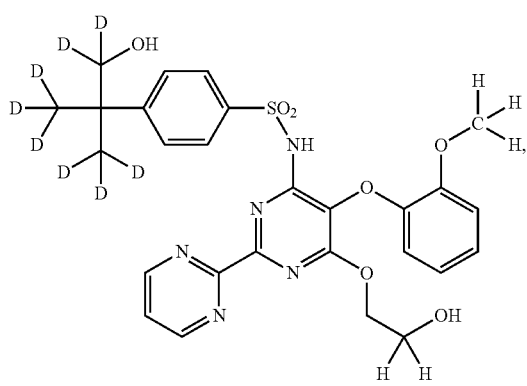
110

111 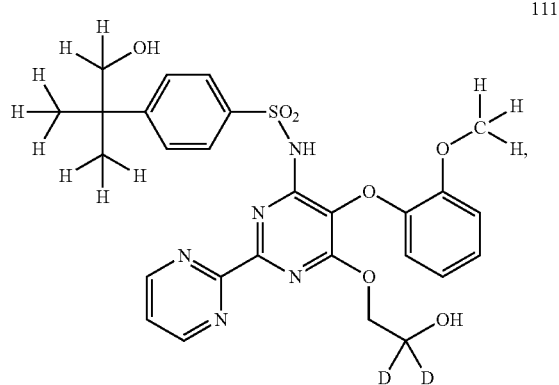
112 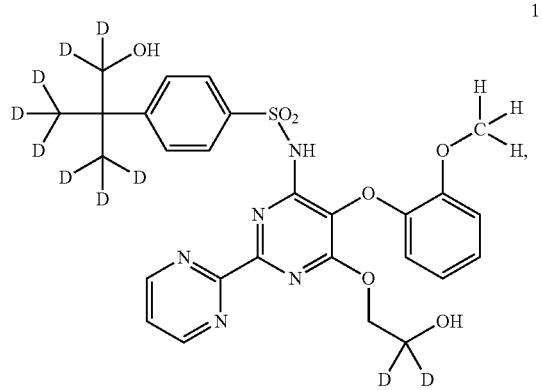
113 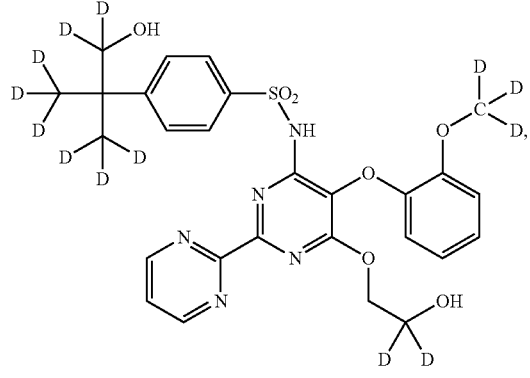
114 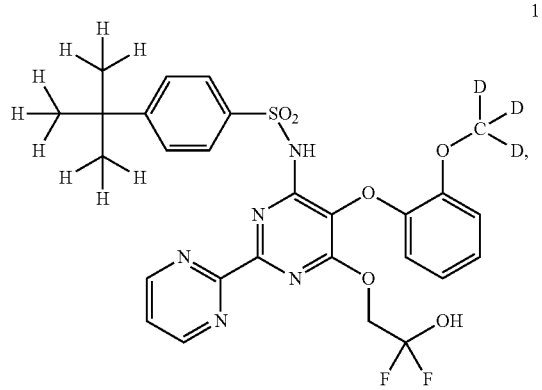
115 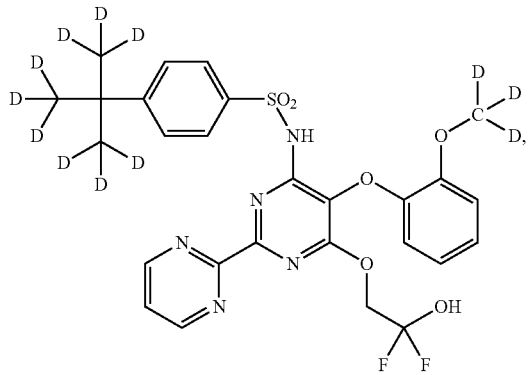
116 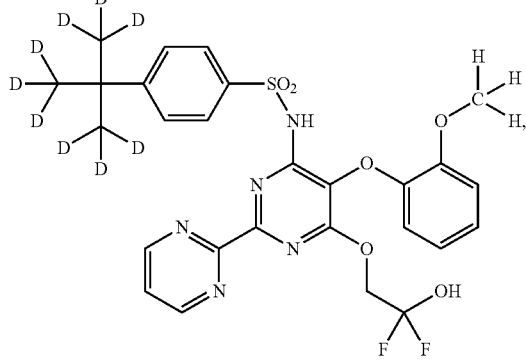
117 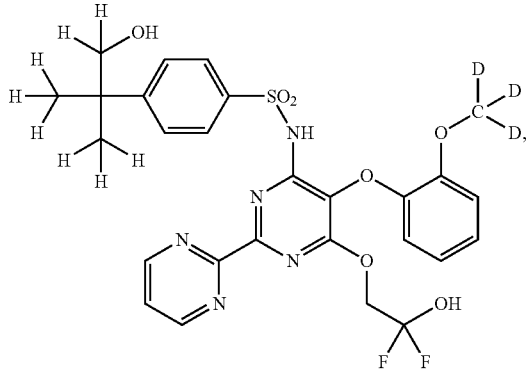
118 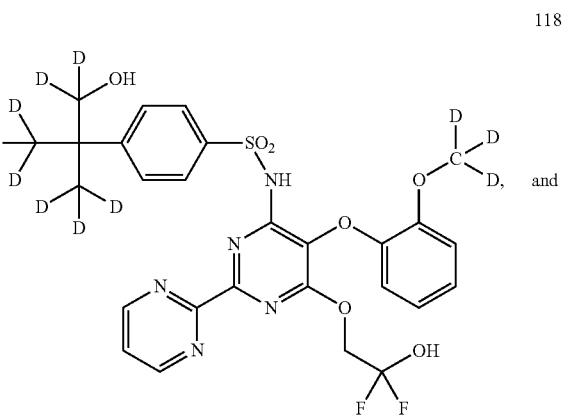
and -continued
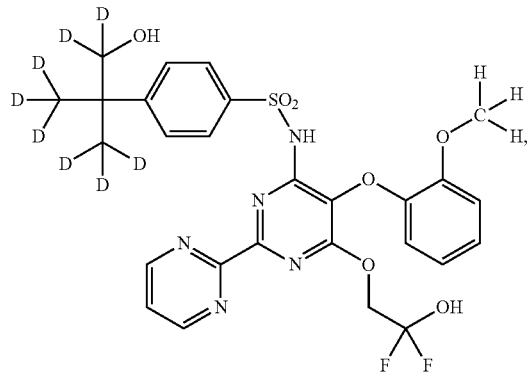
119
or a pharmaceutically acceptable salt thereof.
14. The compound according to claim 1, wherein any atom not specified as deuterium is present in its natural isotopic abundance.
15. A compound selected from:
Compound 101
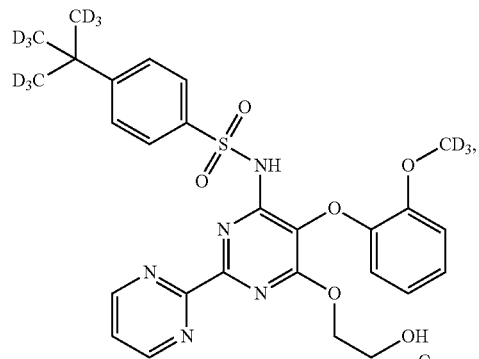
Compound 102
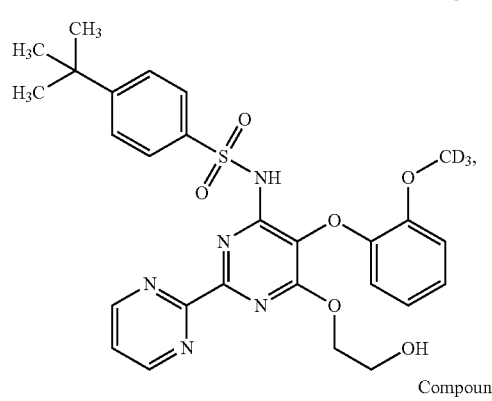
Compound 103
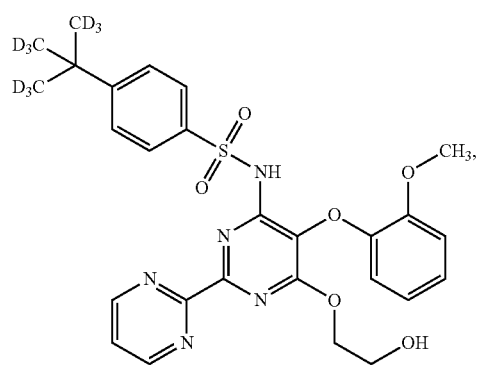
-continued
Compound 104
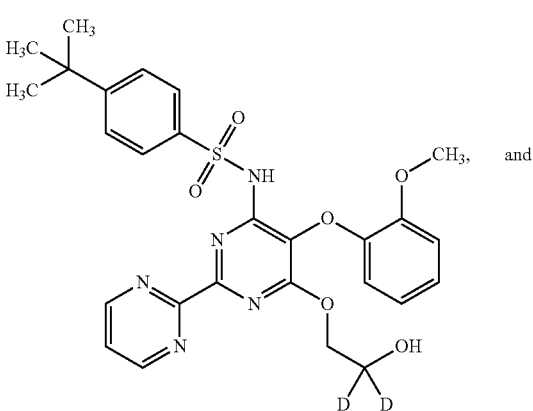
and
Compound 106
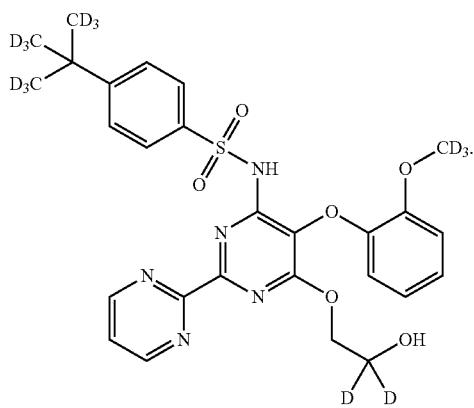
16. A compound of claim 15, wherein the compound is
Compound 101
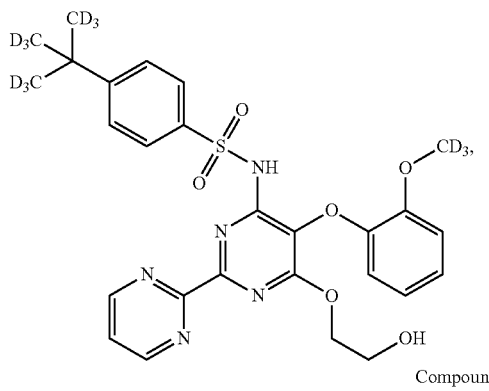
Compound 102
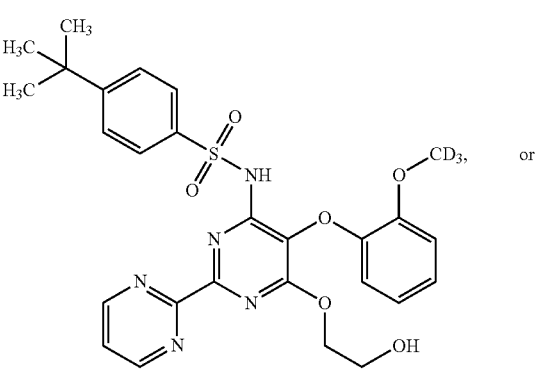
or Compound 106

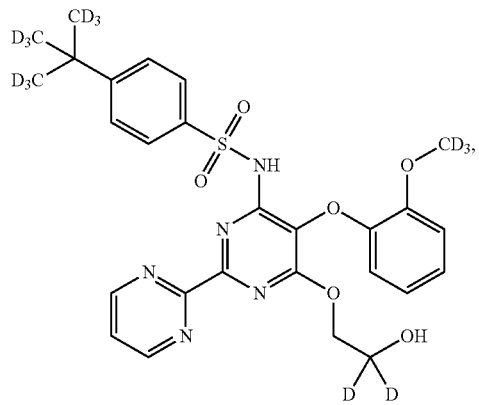

or a pharmaceutically acceptable salt thereof.

17. A compound selected from any one of:

12

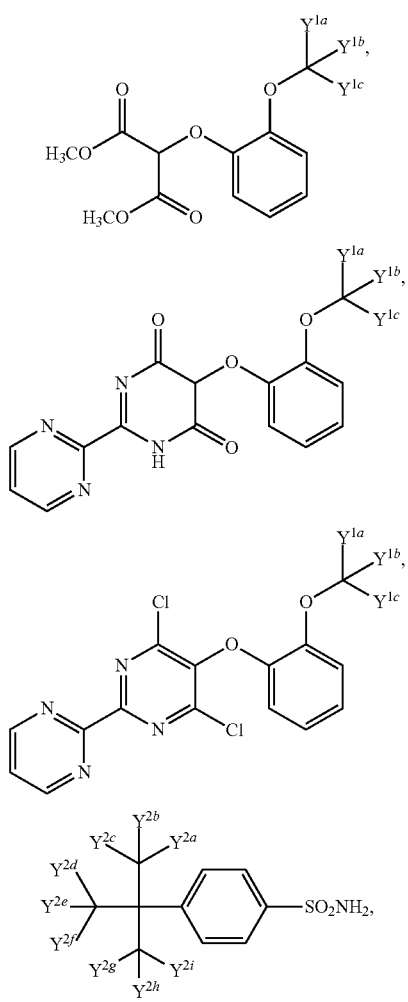

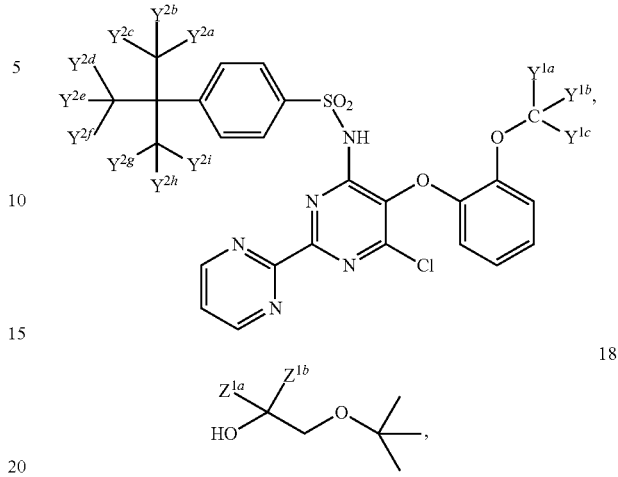

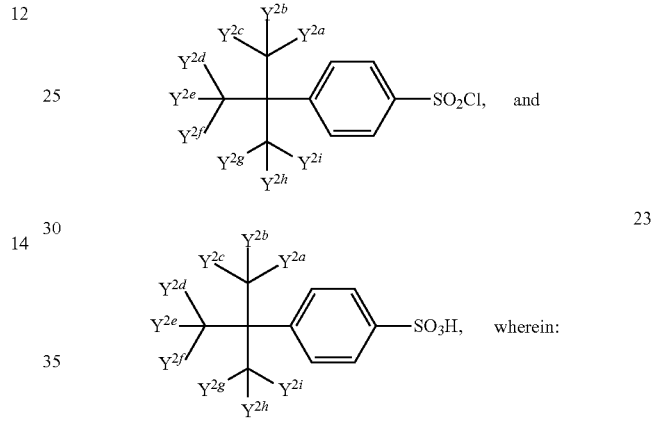

each Y is independently selected from hydrogen or deuterium, and $Y^{2a}$ is additionally selected from OH;

each Z is independently selected from hydrogen, deuterium, or fluorine; and at least one Y or Z is deuterium.

18. The compound of claim 17, wherein the compound has the formula:

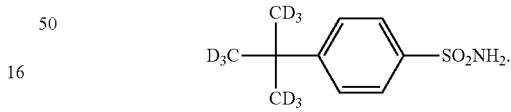

19. A pharmaceutical composition comprising a compound of claim 1; and a pharmaceutically acceptable carrier.

* * * * *

UNITED STATES PATENT AND TRADEMARK OFFICE
CERTIFICATE OF CORRECTION

| | |
|---|---|
| PATENT NO. | : 8,080,549 B2 |
| APPLICATION NO. | : 12/460575 |
| DATED | : December 20, 2011 |
| INVENTOR(S) | : Scott L. Harbeson |

Page 1 of 1

It is certified that error appears in the above-identified patent and that said Letters Patent is hereby corrected as shown below:

In Claim 8, column 38, line 2, please delete "$Y^e$" and insert -- $Y^{2e}$ --.

Signed and Sealed this
Twenty-eighth Day of February, 2012

David J. Kappos
*Director of the United States Patent and Trademark Office*